United States Patent [19]
Cage

[11] Patent Number: 5,423,225
[45] Date of Patent: Jun. 13, 1995

[54] SINGLE PATH RADIAL MODE CORIOLIS MASS FLOW RATE METER

[75] Inventor: Donald R. Cage, Longmont, Colo.

[73] Assignee: Direct Measurement Corp., Longmont, Colo.

[21] Appl. No.: 149,713

[22] Filed: Nov. 9, 1993

Related U.S. Application Data

[63] Continuation of Ser. No. 651,301, Feb. 5, 1991, abandoned.

[51] Int. Cl.$^6$ .............................................. G01F 1/84
[52] U.S. Cl. ............................. 73/861.37; 73/861.18
[58] Field of Search ........... 73/861.37, 861.38, 861.18, 73/702

[56] References Cited

U.S. PATENT DOCUMENTS

| | | | |
|---|---|---|---|
| Re. 31,450 | 11/1983 | Smith | 73/861 |
| 3,485,098 | 12/1969 | Sipin | 73/861.38 |
| 3,927,565 | 12/1975 | Pavlin | 73/861.38 |
| 4,009,616 | 3/1977 | Wonn | 73/703 |
| 4,109,524 | 8/1978 | Smith | 73/194 |
| 4,420,983 | 12/1983 | Langdon | 73/861.18 |
| 4,422,338 | 12/1983 | Smith | 73/861 |
| 4,491,025 | 1/1985 | Smith et al. | 73/861 |
| 4,622,858 | 11/1986 | Mizerak | 73/861 |
| 4,628,744 | 12/1986 | Lew | 73/861 |
| 4,653,332 | 3/1987 | Simonsen | 73/861 |
| 4,680,974 | 7/1987 | Simonsen et al. | 73/861 |
| 4,691,578 | 9/1987 | Herzl | 73/861 |
| 4,716,771 | 1/1988 | Kane | 73/861 |
| 4,729,243 | 3/1988 | Friedland et al. | 73/861 |
| 4,733,569 | 3/1988 | Kelsey et al. | 73/861.38 |
| 4,756,197 | 7/1988 | Herzl | 73/861 |
| 4,756,198 | 7/1988 | Levien | 73/861 |
| 4,768,384 | 9/1988 | Flecken et al. | 73/861 |
| 4,776,220 | 10/1988 | Lew | 73/861 |
| 4,793,191 | 12/1988 | Flecken et al. | 73/861 |
| 4,798,091 | 1/1989 | Lew | 73/861 |
| 4,803,867 | 2/1989 | Dahlin | 73/861.38 |
| 4,811,606 | 3/1989 | Hasegawa et al. | 73/861 |
| 4,813,289 | 3/1989 | Lew | 73/861.38 |
| 4,823,614 | 4/1989 | Dahlin | 73/861 |
| 4,829,832 | 5/1989 | Lew | 73/861.38 |
| 4,831,885 | 5/1989 | Dahlin | 73/861 |
| 4,852,410 | 8/1989 | Corwon et al. | 73/861 |
| 4,856,346 | 8/1989 | Kane | 73/861 |
| 4,869,097 | 9/1989 | Tittmann et al. | 73/703 |
| 4,882,935 | 11/1989 | Lew | 73/861.38 |
| 4,891,991 | 1/1990 | Mattar et al. | 73/861 |
| 4,934,195 | 6/1990 | Hassain | 73/861 |
| 4,949,583 | 8/1990 | Lang et al. | 73/861.37 |
| 5,024,104 | 6/1991 | Daines | 73/861.37 |
| 5,040,415 | 8/1991 | Barkhoudarian | 73/703 |
| 5,044,207 | 9/1991 | Atkinson et al. | 73/861.37 |
| 5,069,075 | 12/1991 | Hansen et al. | 73/861.38 |
| 5,226,330 | 7/1993 | Lew | 73/861.37 |

FOREIGN PATENT DOCUMENTS

| | | | |
|---|---|---|---|
| 0272758 | 12/1987 | Italy . | |
| 62-180741 | 7/1987 | Japan . | |
| 10088617 | 3/1987 | U.S.S.R. | 73/861.37 |

*Primary Examiner*—Sandra L. O'Shea
*Assistant Examiner*—Raymond Y. Mah
*Attorney, Agent, or Firm*—Hitt Chwang & Gaines

[57] ABSTRACT

A flow meter apparatus for measuring the mass flow rate of a fluid using the Coriolis principle. A single straight flow conduit is employed which is vibrated in a radial-mode of vibration. Coriolis forces are thereby produced along the walls of the flow conduits which deform the conduits cross-sectional shape as a function of mass flow rate. Additional embodiments are disclosed employing radial vibration of selected portions of the flow conduit walls.

14 Claims, 16 Drawing Sheets

SINGLE PATH RADIAL MODE CORIOLIS MASS FLOW RATE METER

This is a continuation of application Ser. No. 07/651,301, filed Feb. 5, 1991, now abandoned.

FIELD OF THE INVENTION

This invention relates to Coriolis mass flow rate meters and, in particular, to Coriolis mass flow rate meters using a single straight flow conduit to measure mass flow rate.

BACKGROUND OF THE INVENTION

In the art of Coriolis mass flow rate meters it is well known that a vibrating flow conduit carrying mass flow causes Coriolis forces which deflect the flow conduit away from its normal vibration path proportionally related to mass flow rate. These deflections or their effects can then be measured as an accurate indication of mass flow rate.

This effect was first made commercially successful by Micro Motion Inc. of Boulder, Colo. Early designs employed a single vibrating U-shaped flow conduit which was cantilever mounted from a base. With nothing to counter-balance the vibration of the flow conduit, the design was highly sensitive to mounting conditions and so was redesigned to employ another mounted vibrating arrangement which acted as a counter-balance for the flow conduit similar to that disclosed in their U.S. Pat. Nos. Re. 31,450 and 4,422,338 to Smith. Problems occurred however since changes in the specific gravity of the process-fluid were not matched by changes on the counter-balance, an unbalanced condition could result causing errors. Significant improvement was later made by replacing the counter-balance arrangement by another U-shaped flow conduit identical to the first and splitting the flow into parallel paths, flowing through both conduits simultaneously. This parallel path Coriolis mass flow rate meter (U.S. Pat. No. 4,491,025 to Smith et al) solves this balance problem and has thus become the premier method of mass flow measurement in industry today.

Many other flow conduit geometries have been invented which offer various performance enhancements or alternatives. Examples of different flow conduit geometries are the dual S-tubes of U.S. Pat. Nos. 4,798,091 and 4,776,220 to Lew, the omega shaped tubes of U.S. Pat. No. 4,852,410 to Corwon et al, the B-shapes tubes of U.S. Pat. No. 4,891,991 to Mattar et al, the helically wound flow conduits of U.S. Pat. No. 4,756,198 to Levien, figure-8 shaped flow conduits of U.S. Pat. No. 4,716,771 to Kane, the dual straight tubes of U.S. Pat. No. 4,680,974 to Simonsen et al, and others. All of these geometries employ the basic concept of two parallel flow conduits vibrating in opposition to one another to create a balanced resonant vibrating system.

Although the parallel path Coriolis mass flow rate meter has been a tremendous commercial success, several problems remain. Most of these problems are a consequence of using flow splitters and two parallel flow conduits in order to maintain a balanced resonant system. In addition, most designs employ flow conduits that are curved into various shapes as previously described to enhance the sensitivity of the device to mass flow rate. These two common design features cause a number of problems which preclude the use of Coriolis technology in many applications that would benefit from its use.

Among the problems caused by the flow splitters and curved flow conduits are; (1) Excessive fluid pressure-drop caused by turbulence and drag forces as the fluid passes through the flow splitters and curves of the device. (2) Difficulty in lining or plating the inner surface of geometries having flow splitters and curved flow conduits, with corrosive resistant materials. (3) Inability to meet food and pharmaceutical industry sanitary requirements such as polished surface finish, non-plugable, self-draining, and visually inspectable. (4) Difficulty in designing a case to surround dual curved flow conduits which can contain high rated pressures. (5) Difficulty in designing flow meters for 6" diameter and larger pipelines. (6) Difficulty in reducing the cost of current designs due to the added value of flow splitters, dual flow conduits and curved flow conduit fabrication.

It is therefore recognized that a Coriolis mass flow rate meter employing a single straight flow conduit would be a tremendous advancement in the art. It is the object of the present invention therefore to disclose a means whereby a Coriolis mass flow rate meter can be created using a single straight flow conduit thereby eliminating the problems caused by flow splitters, dual flow paths and curved conduits while retaining the current advantages of balance and symmetry.

SUMMARY OF THE INVENTION

According to the object of the present invention, a Coriolis mass flow rate meter is herein provided utilizing a single straight flow conduit and a unique vibration method thereby eliminating the problems caused by flow splitters and curved flow conduits while retaining the current advantages of balance and symmetry.

The basic operation of a commercially available Coriolis mass flow rate meter according to current art will now be described. Normally two process-fluid filled flow conduits are employed in a parallel-path or serial-path configuration. The two flow conduits form a balanced resonant system and as such are forced to vibrate in a prescribed oscillatory bending-mode of vibration. If the process-fluid is flowing, the combination of fluid motion and conduit vibration causes Coriolis forces which deflect the conduits away from their normal (no flow) paths of vibration proportionally related to mass flow rate. These deflections, or their effects, are then measured as an accurate indication of mass flow rate.

As previously described, only one flow conduit is necessary for measuring mass flow rate in this manner. However, to achieve the superior performance afforded by a balanced resonant system, it's necessary to counter-balance the reaction forces from the forced vibration, thus a second flow conduit is normally employed. For very small meter designs the mass and stiffness properties of the mounting conditions can be sufficiently great to counteract the reaction forces from the forced vibration thereby allowing the use of only one flow conduit. Accordingly, Micro Motion Inc. presently offers only their two smallest flow meters, the model D6 (1/16" line size) and the model D12 (⅛" line size) in a single curved flow conduit configuration.

A single straight flow conduit while solving the aforementioned problems caused by flow splitters and curved conduits, has therefore not been commercially successful in Coriolis mass flow rate meter designs, especially for large flow conduits. This failure is due to the inherent imbalance of a single straight flow conduit in any natural bending-modes of vibration. A straight flow conduit fixedly mounted at both ends has a number of natural bending-modes of vibration wherein the center-line of the conduit deflects or rotates away from its rest position in a number of half sine-shaped waves along the length of the conduit. Higher frequency bending-modes involve increasing numbers of these half sine-shaped waves in integer multiples. Each of these bending-modes causes reaction forces applied to the conduit mounts creating balance and accuracy problems analogous to the single curved flow conduit models previously described. A single straight tube design of this nature is disclosed in U.S. Pat. No. 4,823,614 to Dahlin, in which the flow tube cross-section is permanently deformed in several locations as shown in its FIGS. 2A-2D to enhance its bending in a "higher-mode" such as its FIG. 3B. The higher modes of vibration as shown in the Dahlin patent FIGS. 3A-3E all show the flow conduit bending away from a straight line at its ends which will cause reaction torques, and forces at the mounts. These reactions are not counter balanced and thus can create balance and inaccuracy problems in larger sized meters as previously described. Dahlin states that this embodiment can be used in "average" sized pipes with average being defined as ½ to ¾ inch inside diameter. Although the reason for this size restriction is not explained it is probably a consequence of imbalance from using a bending-mode of vibration with no counter-balance apparatus.

The unique advantages of the present invention accrue from the use of a single straight flow conduit in a radial-mode of vibration instead of a bending-mode as is currently used in the art. For clarity, the term "bending-mode" is defined as a vibration mode wherein the center-line or axis of the flow conduit translates and/or rotates away from its rest position in an oscillatory manner while the cross-sectional shape of the flow conduit remains essentially unchanged. By contrast, the term "radial-mode" is defined as a vibration mode wherein the center-line or axis of the flow conduit remains essentially unchanged while all or a part of the wall of the flow conduit translates and/or rotates away from its rest position in an oscillatory manner. Common examples of radial-modes of vibration are the natural vibration of a bell or wine glass. In these two examples the fundamental radial-mode of vibration causes the normally round cross-sectional shape of the free end of the bell or wine glass to deflect into an oscillating elliptical shape. Since the center-line or axis of this radial-mode stays essentially unchanged, the stem (in the wine glass example) can be held without feeling or interfering with the vibration, exemplifying the absence of reaction forces at the mount. Applying this idea to the flow conduit of a Coriolis mass flow rate meter, a single straight flow conduit is employed, fixedly attached at both ends, and vibrated in a radial-mode of vibration where the wall of the flow conduit translates and/or rotates away from its rest position in an oscillatory manner, and the center-line of the flow conduit remains essentially unchanged. The combination of fluid motion and radial-mode vibration causes a Coriolis force distribution along the moving wall of the flow conduit which alters the cross-sectional shape of the conduit as a function of mass flow rate. This altered shape or its effects, are then measured as an accurate indication of mass flow rate. Since this radial mode of vibration causes substantially no net reaction forces where the conduits are mounted, a balanced resonant system Coriolis mass flow rate meter is thereby created with no flow splitters, curved flow conduits, or counter-balance devices.

In addition, a unique non-intrusive method is employed to determine the pressure inside the flow conduit by simultaneously vibrating the flow conduit in two modes of vibration. The ratio of the frequencies of the two modes of vibration is functionally related to the pressure difference between the inside and the outside of the flow conduit.

As an alternate to using a radial-mode of vibration involving the entire wall of the flow conduit as previously described, a portion of the flow conduit perimeter can be vibrated as necessary to generate Coriolis forces. This method is well suited for use in flow conduits of very large size and non-circular shapes where vibration of the entire conduit is not practical. This method is also well suited to flow conduits formed into bulk materials thus having several rigid sides incapable of entire-perimeter radial mode vibration, such as a flow conduit etched into silicon or quartz to form a micro flow meter.

The present invention solves the previously mentioned problems caused by flow splitters, curved flow conduits and imbalance, and allows Coriolis mass flow meter technology to be used in areas such as sanitary applications, gas flow, air flow meters for weather stations, airplanes, and low pressure air-duct systems, micro flow meters, liquid flow meters for residential, industrial, oceanographic and shipboard use, and many more.

BRIEF DESCRIPTION OF THE DRAWINGS

The invention may be better understood from the following detailed description thereof taken in conjunction with the drawing in which.

DETAILED DESCRIPTION OF THE INVENTION

Figure 1:
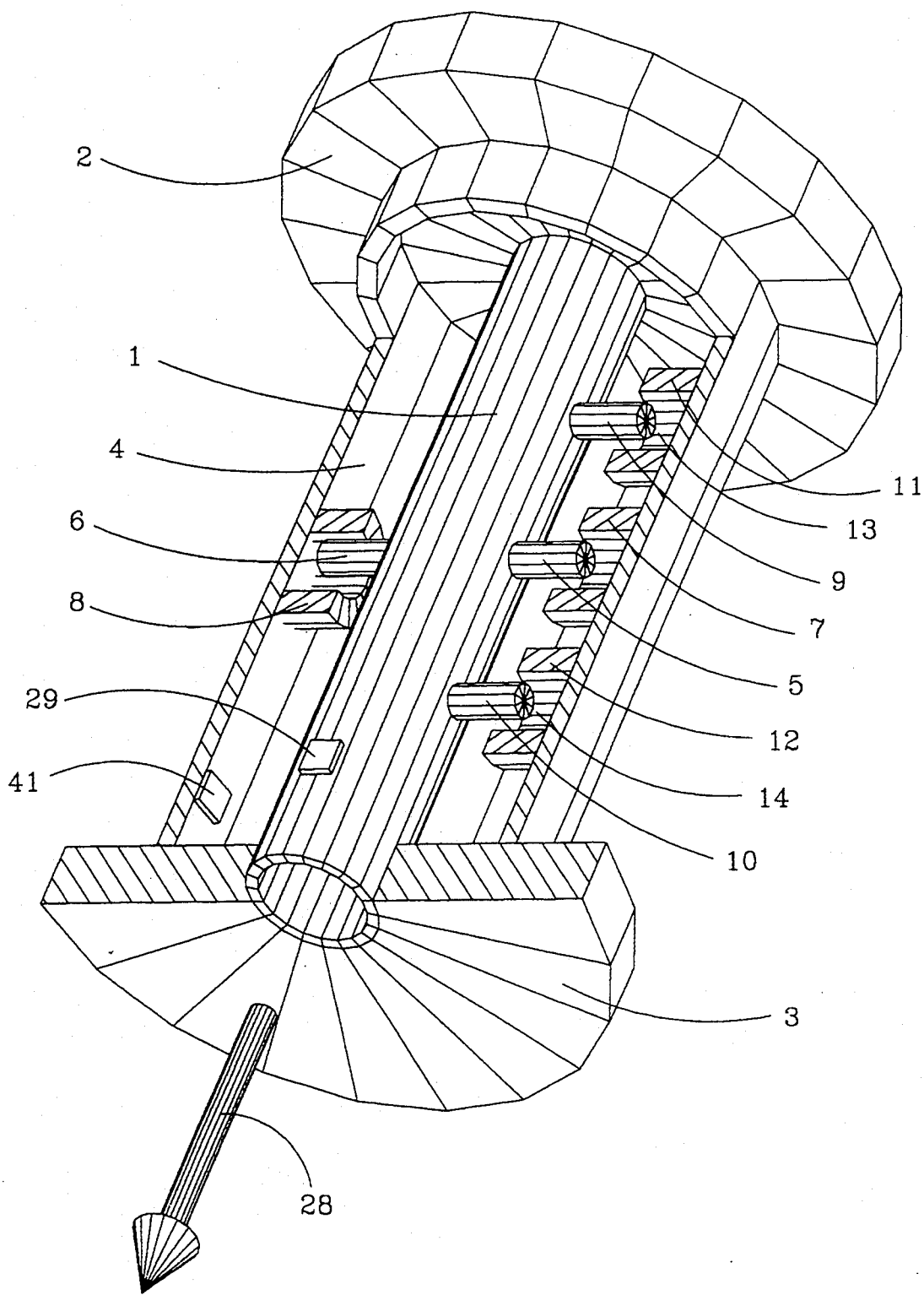
FIG. 1 is a perspective view of one possible preferred exemplary embodiment of the present invention with a portion of the outer case cut away for viewing the apparatus inside.

FIG. 1 shows a perspective view of one preferred exemplary embodiment of the present invention. This embodiment comprises a single straight flow conduit 1 preferably made of a strong flexible non-corrosive material such as titanium. Alternate materials with properties that enhance performance characteristics such as flexibility, corrosion resistance, fatigue strength, constant elastic modulus, low expansion rate, and others can also be used. These alternate materials include 300 series stainless steels, Inconel, Nispan-C and Monel by International Nickel Company, alloys of Hasteloy by the Cabot Corporation, aluminum, beryllium copper, latex rubber, fiberglass, acrylic, quartz and others. In addition, the inner surface of conduit 1 can be subsequently lined or plated with a non-corrosive material such as nickel, gold, zirconium, fluoropolymers such as Teflon by Dupont, and others.

Flow conduit 1 is fixedly attached at its ends to manifolds 2 and 3, preferably by a welding or brazing process. It is anticipated that manifolds 2 and 3 can be designed in a variety of configurations such as standard pipe flanges, threaded pipe fittings, sanitary fittings, quick-connect fittings, extended tubes, hydrodynamically or aerodynamically shaped openings, and others. It is further anticipated that manifolds will normally be used for convenience of mounting the device or its parts, however manifolds are not necessary for the operation of the device. Accordingly, a portion of an existing pipeline could be instrumented and vibrated in a radial-mode vibration to create the requisite Coriolis forces without the aid of manifolds, however, Since existing pipelines can have inappropriate geometric and material properties for this service, it is not the preferred method.

Mounted in association with flow conduit 1 is temperature sensor 29 which is preferably a platinum resistance thermal device (RTD), however many other types of temperature sensors could be used such as thermocouples, semiconductor sensors, optical and others. If a flow conduit material is used with an elastic modulus that changes as a function of temperature, the sensitivity of the device to mass flow rate can also change-related to temperature. This effect car be negated by compensating the final flow rate output signal (19 of FIG. 16) functionally related to the temperature of flow conduit 1.

Concentrically arranged around flow conduit 1 is case 4, preferably made of a strong low-corrosion material such as 300 series stainless steel pipe. Some of the possible design considerations of case 4 are to protect conduit 1 and its components from ambient conditions, to contain process fluid in case of a leak, to minimize the effect of stresses on conduit 1 caused by mounting conditions, to contain a prescribed amount of pressure to extend the pressure range or alter the sensitivity of flow conduit 1 to mass flow rate, to convey purging gas to the components inside, to contain a vacuum around conduit 1, for mounting the motion drivers and sensors, and others. A wide variety of possible case materials and configurations are thus anticipated depending on desired performance characteristics. Some alternate materials for case 4 include alloy, or carbon steel, aluminum, brass, quartz, glass, plastic and others. Case 4 is fixedly attached at its ends to manifolds 2 and 3 preferably by a welding or brazing process thus forming a simple protective vessel surrounding the flow conduit. It is anticipated that a case will normally be used, however, it is not necessary for the operation of the device.

A temperature difference between conduit 1 and case 4 can cause a thermally induced expansion difference which can create axial stress in conduit 1. This axial stress can alter the sensitivity of conduit 1 to mass flow rate.

Figure 24:
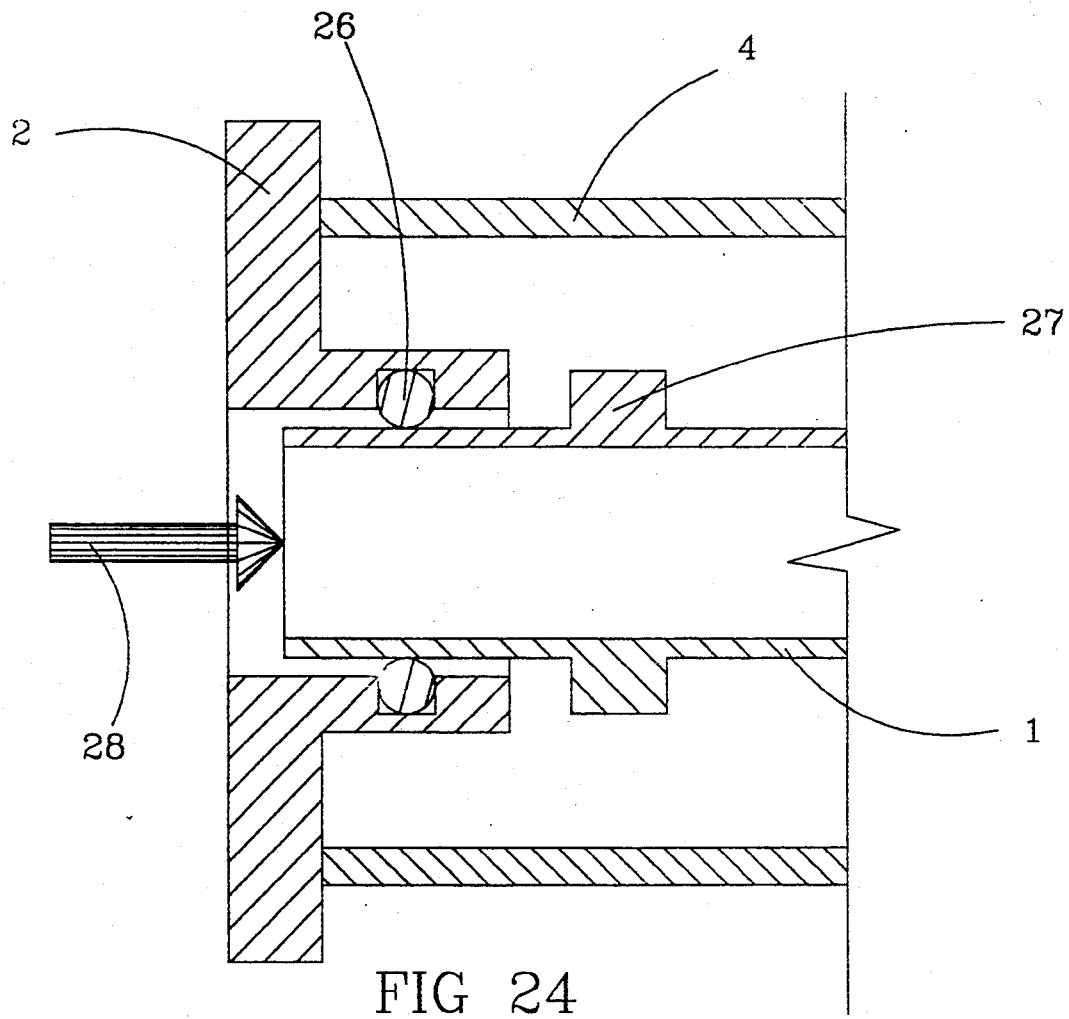
FIG. 24 is a cross-sectional view of an exemplary stress decoupling joint used to eliminate axial stress from the flow conduit.

This effect as well as mounting induced axial stress effects can be negated by mounting at least one end of conduit 1 to a slip-joint or flexible joint incapable of bearing axial stress such as shown in FIG. 24 where conduit 1 is slipped through an o-ring seal 26 in manifold 2 and therefore pipeline stress is transmitted around conduit 1 through manifold 2 and case 4. In this arrangement, a stiffener 27 would preferably be used to isolate the radial vibration of conduit 1 along a selected portion of conduit 1 and away from the slip-joint area. Stiffener 27 could also be used for this vibration isolation purpose without being associated with a slip-joint or flexible joint, to effectively isolate the radial vibration along a selected portion of the flow conduit.

This thermally induced axial stress effect can also be minimized by using a material for both case 4 and conduit 1 with a low coefficient of thermal expansion such as quartz or Invar 32-5 by Carpenter Technology Corporation. Since using low-expansion materials for both case 4 and conduit 1 is not always practical, the method employed in the preferred exemplary embodiment of FIG. 1 is to determine the temperature difference between case 4 and conduit 1, then compensate the final output signal 19 of FIG. 16, functionally related to this temperature difference. Accordingly, mounted in association with case 4 is temperature sensor 41 which is preferably a platinum resistance thermal device (RTD), however many other types of temperature sensors could be used. Temperature sensor 41 is used in conjunction with temperature sensor 29 to determine the temperature difference between case 4 and conduit 1.

A pressure difference between the inside and the outside of flow conduit 1 can cause stress which can alter the stiffness and thus the sensitivity of the flow conduit to mass flow rate. For low pressure applications this effect can usually be neglected. For higher pressure applications, the effect can be negated by applying a prescribed pressure to the area between case 4 and conduit 1 using a fluid such as argon, nitrogen, air, helium, or the process fluid itself, to eliminate or maintain a prescribed amount of stress in conduit 1. In the preferred exemplary embodiment of FIG. 1 a unique method is employed to non-intrusively measure and compensate for this pressure effect using the vibration of flow conduit 1. One observable effect from increasing the pressure difference between the inside and the outside of flow conduit 1 is to increase the frequencies of most of its natural modes of vibration. The amount of frequency increase varies for each mode of vibration and, in general, becomes less for higher frequency modes. Therefore, by finding the ratio of two prescribed modes of vibration, the pressure difference can thus be determined. Accordingly, conduit 1 is forced to vibrate in two radial modes of vibration to both measure mass flow rate and to determine pressure difference as shall further be explained.

Positioned approximately half way between manifolds 2 and 3 and fixedly attached to conduit 1, are driver magnets 5 and 6 which are arranged diametrically opposite to each other. Magnets 5 and 6 are preferably made of alloys of samarium-cobalt or alnico and can be used with or without a keeper. Associated with magnets 5 and 6 are driver coils 7 and 8 respectively which are fixedly attached to case 4 and are used in conjunction with magnets 5 and 6 to drive conduit 1 into two prescribed radial-modes of vibration. Only one magnet-coil driving source is necessary, however, using two magnet-coil pairs in this manner improves symmetry and balance. Other drive means could be employed to force the requisite radial-mode vibrations such as electroded surfaces on conduit 1 interacting with similar electrodes on the inner surface of case 4, or piezoelectric bender elements, mechanical actuators, and others. In addition, if a ferromagnetic material is used for conduit 1, electromagnetic drivers can be used to force the requisite vibration without the addition of any device fixed to the conduit.

Located part way between driver magnet 5 and manifolds 2 and 3 are pickoff magnets 9 and 10 respectively which are preferably made of alloys of samarium-cobalt or alnico and are fixedly attached to conduit 1. Arranged in association with pickoff magnets 9 and 10 are pickoff coils 11 and 12 respectively which are fixedly attached to case 4. Magnet 9 and coil 11 collectively form motion detector 13 which senses the motion of conduit 1 at its location. Magnet 10 and coil 12 collectively form motion detector 14 which senses the motion of conduit 1 at its location. The preferred exemplary embodiment employs magnets and coils as motion detectors however many other types of motion detectors have been successfully tested or anticipated such as strain gages, accelerometers, optical transducers, capacitive transducers, piezoelectric and inductive sensors, and others. Other locations for motion detectors can also be successfully utilized with the requirement that if two motion detectors are used, they are separated from each other by some distance along the length of conduit 1.

Figure 2:
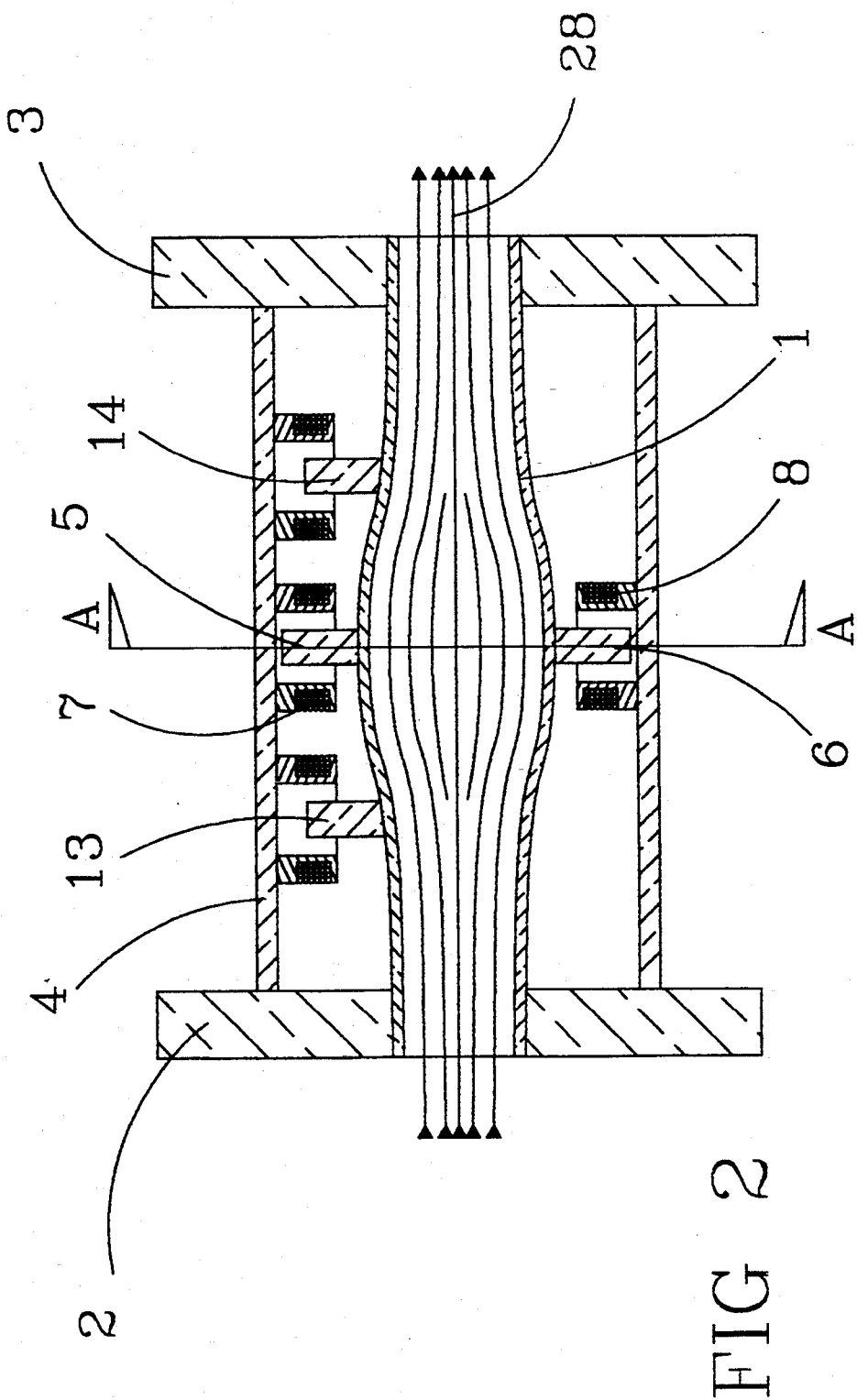
FIG. 2 is a cross-sectional view of the embodiment of FIG. 1 showing the radial-mode vibration shape of the flow conduit where it has reached its peak deflection in the vertical direction. The cross-section of this view along line A—A is shown in FIG. 5.
Figure 3:
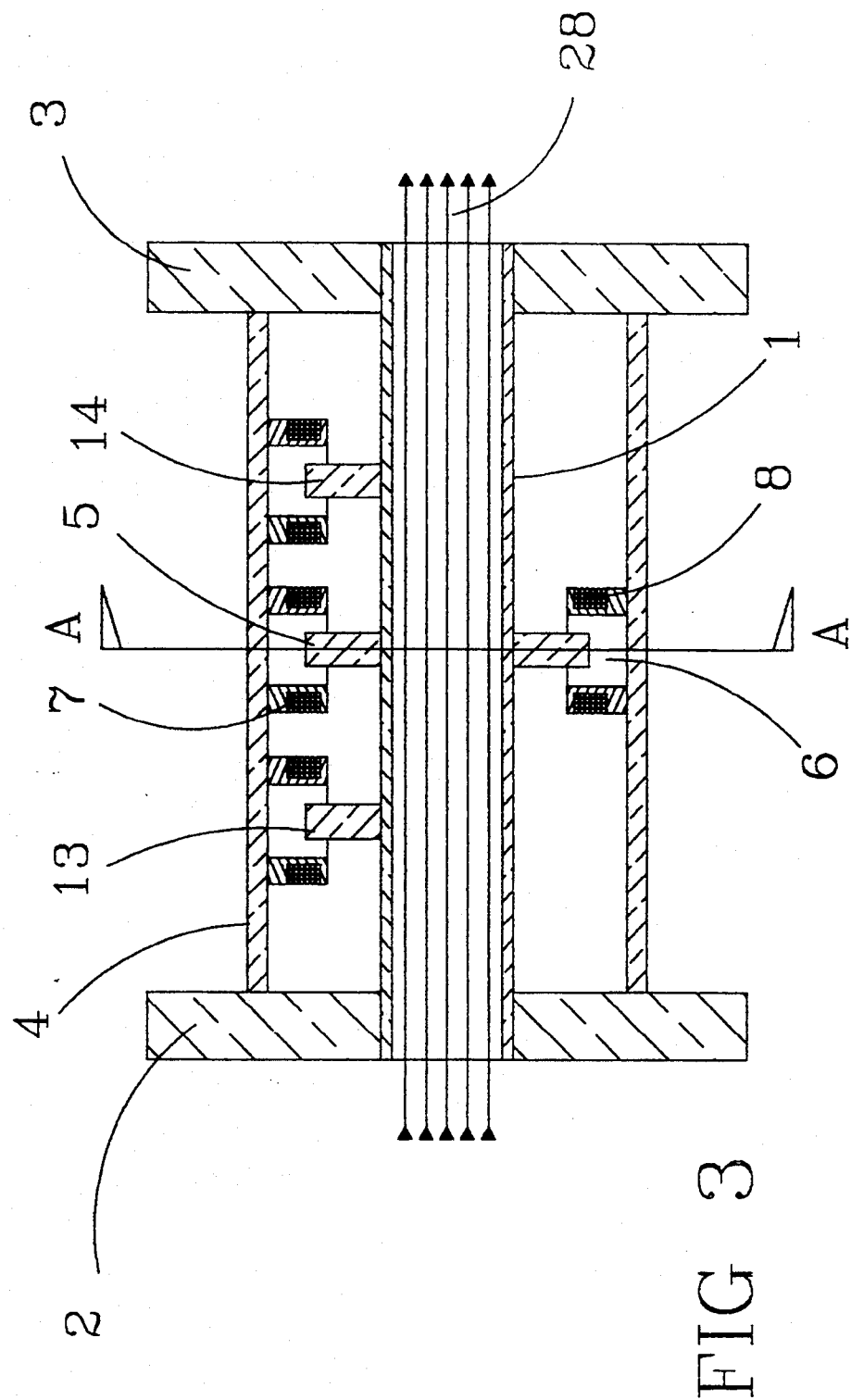
FIG. 3 is a cross-sectional view of the embodiment of FIG. 1 showing the radial-mode vibration shape of the flow conduit where it has reached its undeflected center position. This is also representative of the flow conduits' rest position. The cross-section of this view along line A—A is shown in FIG. 6.
Figure 4:
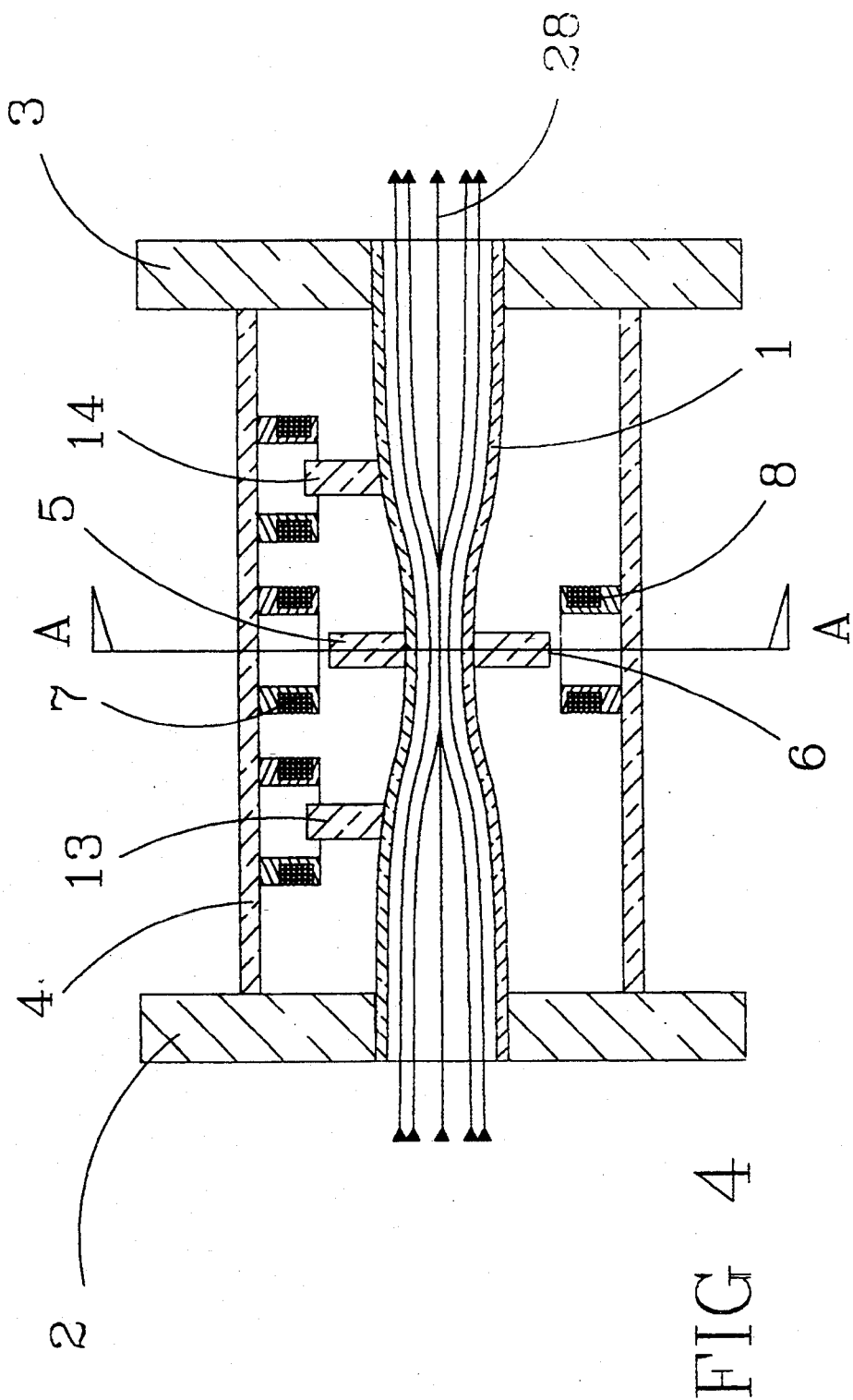
FIG. 4 is a cross-sectional view of the embodiment of FIG. 1 showing the radial-mode vibration shape of the flow conduit where it has reached its peak deflection in the horizontal direction. The cross-section of this view along line A—A is shown in FIG. 7.
Figure 5:
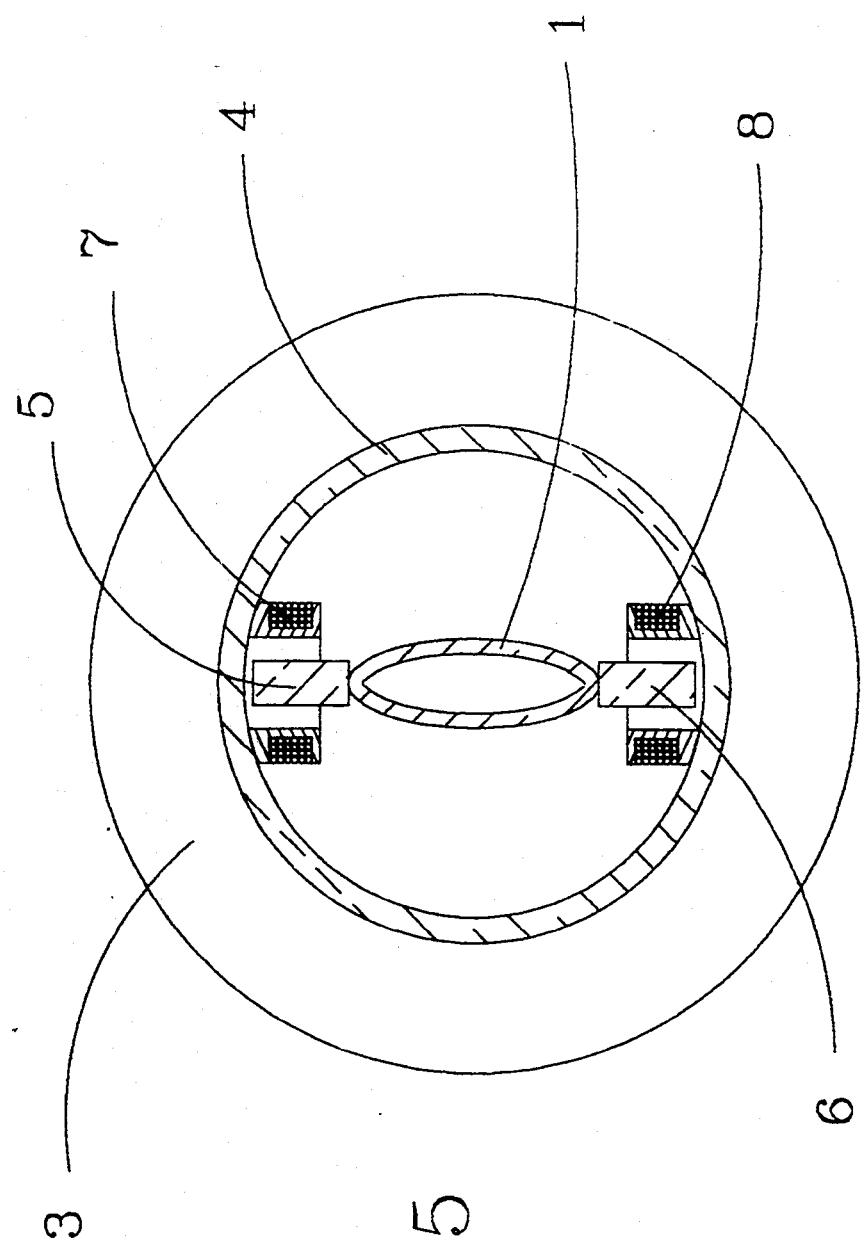
FIG. 5 is a cross-sectional view along section A—A in FIG. 2 showing the elliptical cross-sectional shape of the flow conduit at its peak deflection in the vertical direction.
Figure 6:
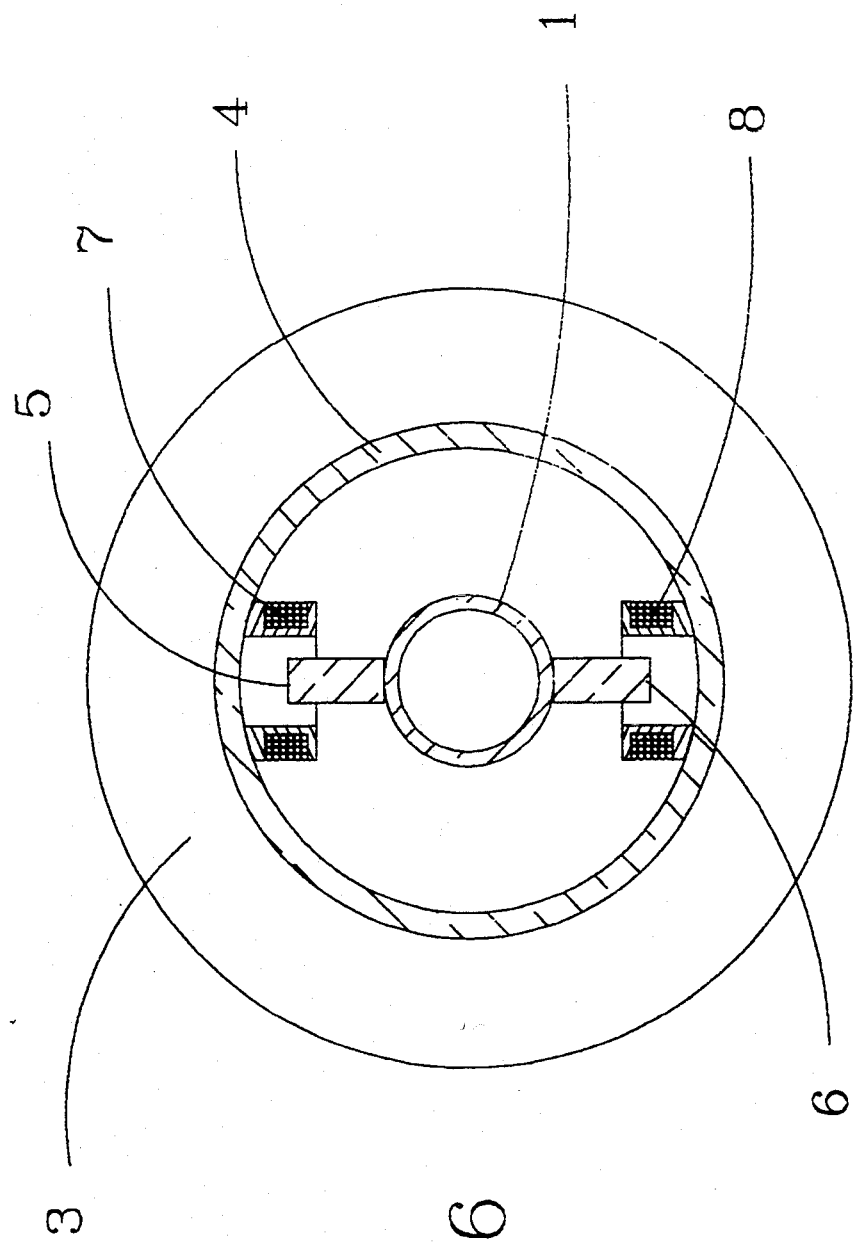
FIG. 6 is a cross-sectional view along section A—A of FIG. 3 showing the circular cross-sectional shape of the flow conduit as it passes through its undeflected center position.
Figure 7:
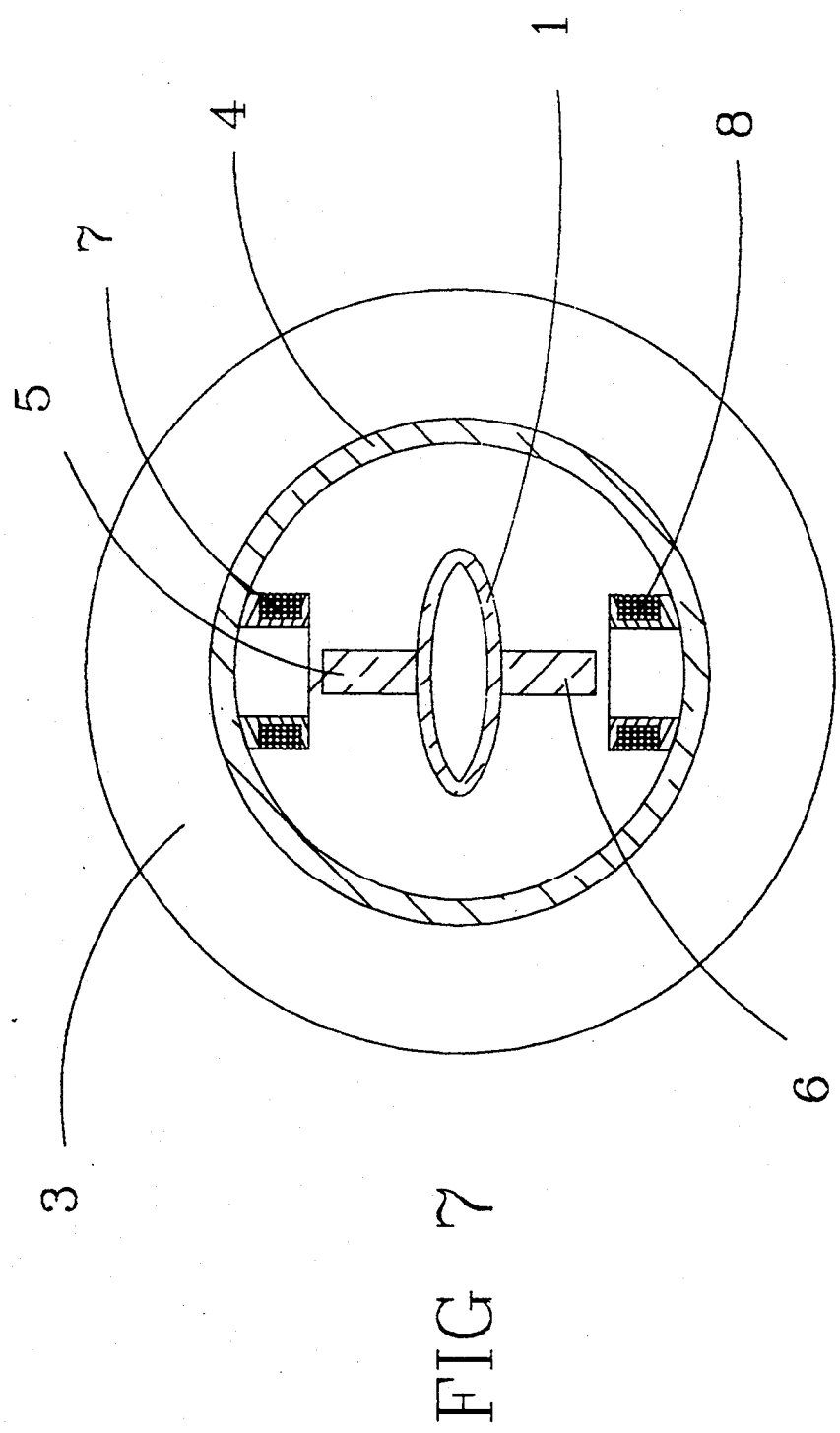
FIG. 7 is a cross-sectional view along section A—A in FIG. 4 showing the elliptical cross-sectional shape of the flow conduit at its peak deflection in the horizontal direction.
Figure 10:
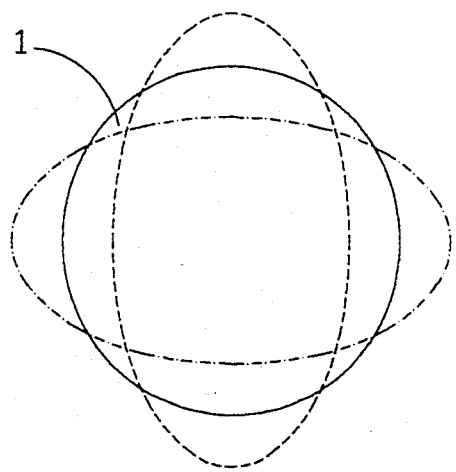
FIG. 10 is a cross-sectional representation of the two-lobe radial-mode vibration of the flow conduit in the preferred exemplary embodiment of FIG. 1 shown with three sequential deflected shapes (peak vertical, undeflected, peak horizontal) superimposed on each other.
Figure 13:
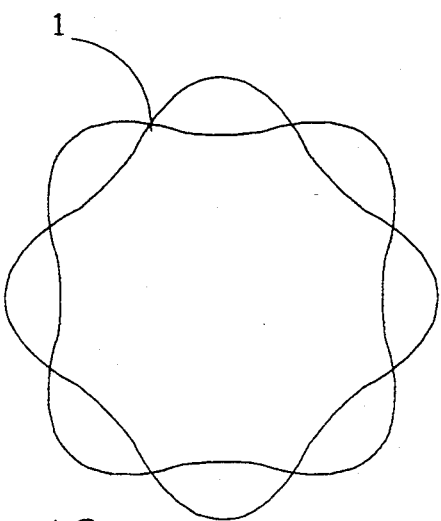
FIG. 13 is cross-sectional representation of an alternate radial-mode of vibration to that shown in FIG. 10 with two sequential deflected shapes superimposed on each other. This is a four-lobe mode, and also the preferred secondary mode of vibration to determine pressure.
Figure 16:
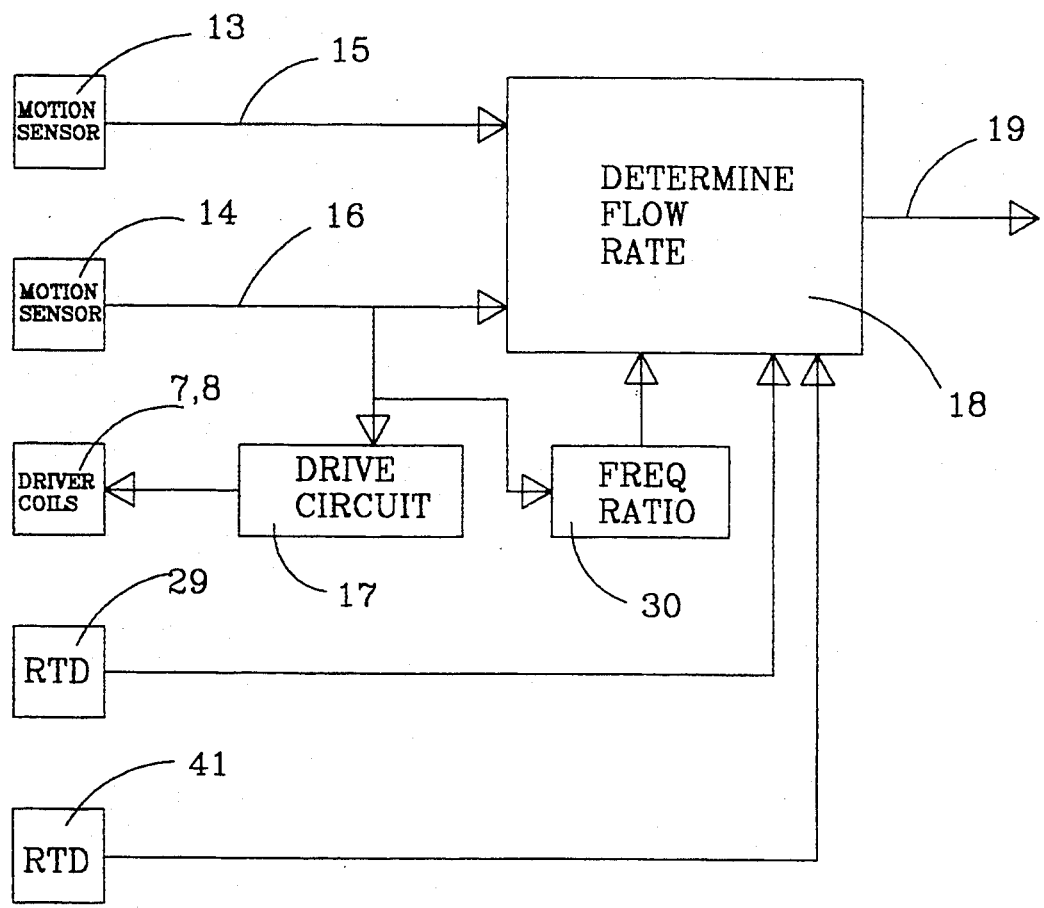
FIG. 16 is a block diagram of one possible configuration of circuit components used to measure mass flow rate according to the present invention.

The operation of the preferred exemplary embodiment shall now be described. Driver coils 7 and 8 are electrically excited to produce two simultaneous radial-mode vibrations. The primary mode is the two-lobe mode as shown in FIGS. 2 through 7 and in FIG. 10, which depict the sequence of conduit motion from elliptically elongated in the vertical direction (FIGS. 2 and 5) through a round undeflected shape (FIGS. 3 and 6) to being elliptically elongated in the horizontal direction (FIGS. 4 and 7). FIG. 10 shows the same sequence of three cross sectional shapes of conduit 1 superimposed on each other. The amplitude of elliptical deformation progresses from zero deformation at the fixed ends of conduit 1 to a maximum deformation near the center at drive magnets 5 and 6. This change in amplitude of the radial vibration along the length of flow conduit 1 is necessary to cause the requisite Coriolis forces for mass flow measurement. The secondary vibration mode is preferably the four-lobe mode as shown in FIG. 13. The primary mode is used to cause the requisite Coriolis forces and as such is maintained at a sufficiently high amplitude limited by material, fatigue and stress factors. The secondary mode is used as a reference frequency to determine the pressure difference across the wall of flow conduit 1 and is therefore maintained at a minimum detectable level so as not to interfere with or significantly contribute to the motion detector signals 15 and 16. These vibrations are maintained by using signal 16 from motion detector 14 in a feed-back loop to circuit component 17 as shown in FIG. 16 which in turn applies a reinforcing signal to driver coils 7 and 8 with energy at the appropriate frequencies and phases to maintain the prescribed vibrations. As an alternate to maintaining the secondary vibration mode continuously for pressure difference determination, it can be turned on and off as necessary in a sampling technique.

Figure 14:
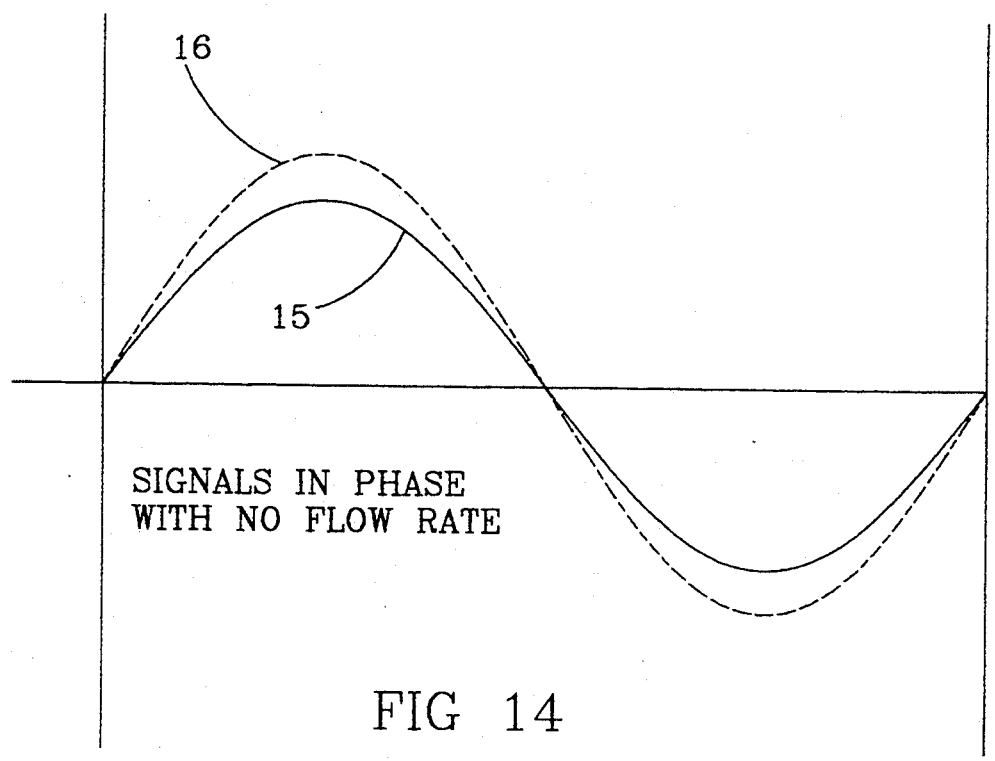
FIG. 14 is a representation of the time relationship of signals from the motion detectors of FIG. 1 with no fluid flowing through the flow conduit.
Figure 15:
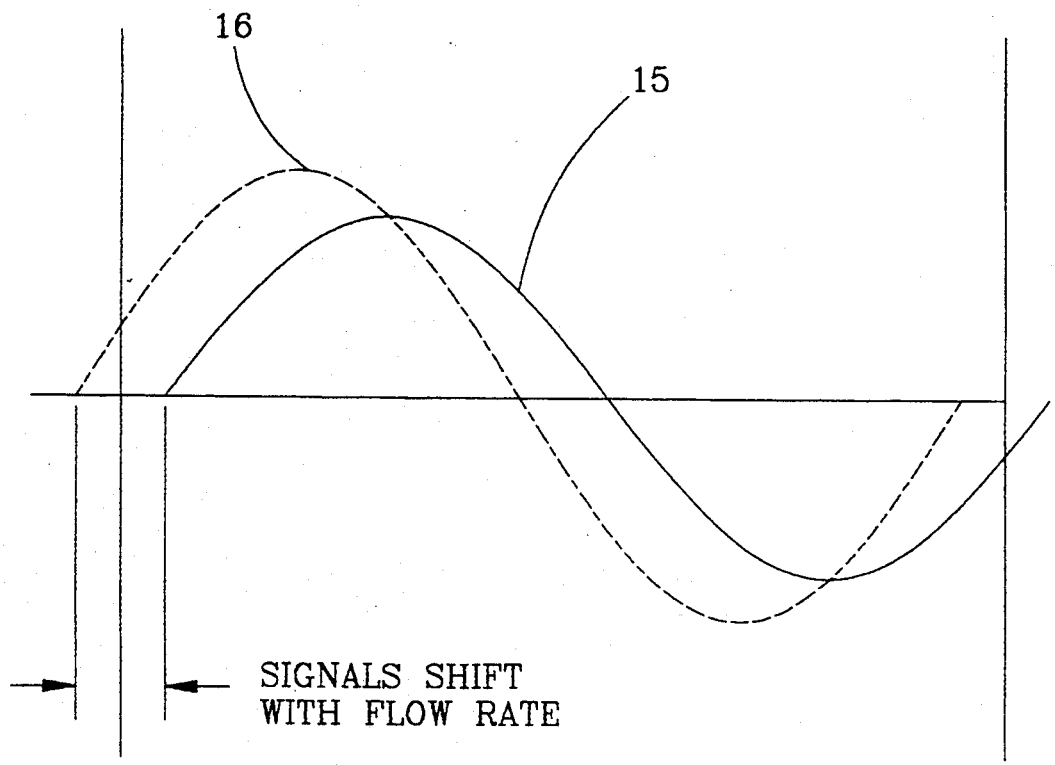
FIG. 15 is a representation of the time relationship of signals from the motion detectors of FIG. 1 with fluid flowing through the flow conduit.

Once the desired motion is established, motion detectors 13 and 14 will produce essentially sinusoidal signals 15 and 16 at the frequency of the primary vibration, and substantially equal in phase when no fluid is flowing in conduit 1 as shown in FIG. 14. When process-fluid flows through conduit 1, the direction of the fluid velocity changes to track the shape of the conduit during its radial-mode vibration. Referring to FIG. 2, the direction of fluid 28 entering from the left side is essentially parallel with the axis of conduit 1 as it passes through manifold 2. Between manifold 2 and driver magnet 5, fluid 28 (along the upper and lower surfaces of flow conduit 1) diverges away from the conduit center-line to track the shape of conduit 1. As the fluid 28 passes under drive magnet 5 its direction is again parallel with the axis of conduit 1. Between drive magnet 5 and manifold 3, fluid 28 converges toward the conduit center-line. Upon reaching manifold 3 fluid 28 is again moving parallel with the axis of conduit 1. As the elliptical deformation of conduit 1 passes through its circular (undeflected) shape as in FIG. 3, all the fluid 28 is shown parallel to the center-line of conduit 1. FIG. 4 shows conduit 1 at its peak deflection in the horizontal direction. In this figure, fluid 28 along the top and bottom surfaces entering from the left, first converges toward the center-line of conduit 1, then becomes parallel to the axis of the conduit as it passes below drive magnet 5, then diverges away from center-line toward the right side of conduit 1, and finally exiting in a parallel direction. FIGS. 2 and 4 clearly show the change in direction of the fluid 28 along the top and bottom surfaces of flow conduit 1 however, since these figures show the conduits peak deflections, the conduit motion is essentially stopped at these positions thus causing no Coriolis forces. It is when conduit 1 passes through its center position of FIG. 3 that its shape is changing most rapidly and thus can cause the greatest Coriolis forces. Coriolis forces will thus be produced proportionally related to the mass of the moving fluid, its velocity, and the rate of change of its direction. Since the rate of change in the fluid direction along the top surface of conduit 1 is opposite to that along the bottom surface, a Coriolis force distribution along the upper and lower surfaces of conduit 1 is thereby created similar to that shown in FIG. 8. The fluid motions and Coriolis force distributions just described pertained to the upper and lower surfaces of conduit 1, however, during the forced radial-vibration the sides of conduit 1 move in the opposite sense to the upper and lower surfaces. Accordingly, another similar Coriolis force distribution will also be caused along the sides (90° from the top and bottom surfaces) of conduit 1 with the direction of forces reversed (not shown). All these Coriolis force distributions reach a maximum value and thus will most greatly alter the shape of conduit 1 as it passes through its normally circular position (FIG. 3). One measurable effect of these forces is to deform conduit 1 into a shape similar to that shown in FIGS. 9 through 9C where the amount of deformation shown is greatly exaggerated for clarity. This deformation thereby causes a difference between signals 15 and 16 which can then be measured in a variety of ways as an accurate indication of mass flow rate. One measurable effect of this deformation is to delay the phase or time relationship of the radial-mode vibration toward the fluid entry end of conduit 1, and advance the phase or time relationship of the radial-mode vibration toward the fluid exit end of conduit 1. In the preferred exemplary embodiment therefore, this phase or time relationship is used to measure mass flow. This effect will cause signal 16 to precede signal 15 in time by an amount that is a function of mass flow rate, as shown in FIG. 15. Signals 15 and 16 are then applied to circuit component 18 of FIG. 16 which compares the phase or time difference between signals 15 and 16, and according to a prescribed function, creates an output signal 19 proportionally related to mass flow rate.

Figure 23A:
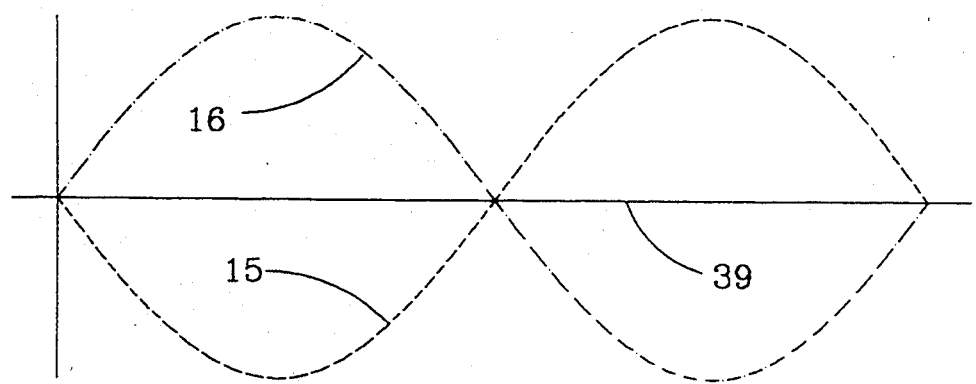
FIG. 23A is a representation of the signals from the motion detectors of FIG. 1, and their sum with one of the signals inverted and with no flow through the flow conduit.
Figure 23B:
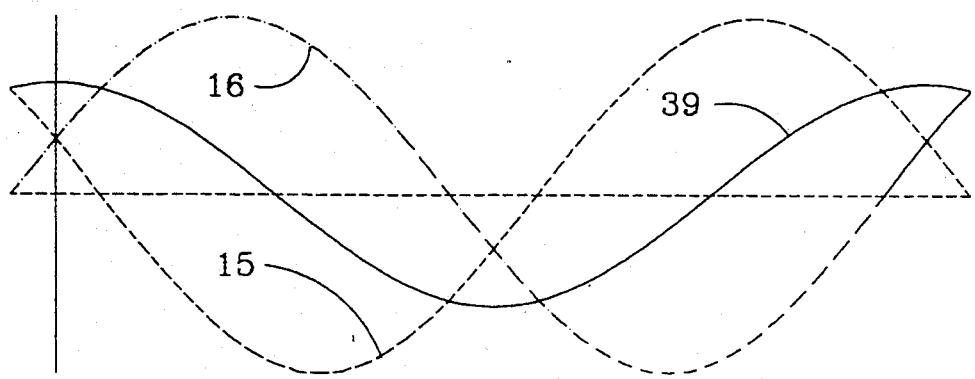
FIG. 23B is a representation of the signals from the motion detectors of FIG. 1, and their sum with one of the signals inverted and with flow through the flow conduit.

Another way to utilize motion detector signals 15 and 16 to measure mass flow rate is to invert one of the signals (180° phase shift) then add them both together, as shown in FIG. 23A. If there is no fluid flow through conduit 1 and the amplitudes of signals 15 and 16 are the same, the resulting sum 31 will be zero or a DC value. With fluid flow in conduit 1, the phase relationship between signals 15 and 16 will change as shown in FIG. 23B causing their sum 31 to be a resultant sine-wave whose amplitude is related to mass flow rate, and whose phase is related to fluid flow direction through conduit 1.

Another method to determine mass flow rate is to maintain the driven amplitude to be a constant value and measure the amplitude of either motion detector signal (15 or 16). The amplitude of the motion sensed at the fluid entry end of conduit 1 (signal 15) will be slightly reduced while the amplitude at the fluid exit end of conduit 1 (signal 16 will be slightly greater, as a function of mass flow rate. Using this method only a single motion detector is required for operation, however using both signals 15 and 16 doubles the available measurement and would thus be preferable. Many other methods that utilize a change in one or both of the motion detector signals to determine mass flow rate have been successfully tested or anticipated.

Circuit component 30 of FIG. 16 accepts input from motion detector signal 16 and determines the ratio of the primary frequency to the secondary frequency of conduit 1. This can be done using filter circuits to isolate the individual frequencies and then employing timing circuits to measure their periods, digital techniques involving Fast Fourier Transforms (FFT), and others.

Component 30 then provides a signal proportional to this frequency ratio to circuit component 18. Component 18 also accepts input from temperature sensors 29 and 41 and compensates the final output signal 19 as necessary to correct for the effects of temperature, thermally induced axial stress, and pressure difference. The final output signal 19 can then be used as an accurate indication of mass flow rate by other equipment for purposes such as monitoring flow rate, controlling valves, proportional mixing, batching, and others.

The initial non-flow phase relationship (zero phase difference in this example) of signals 15 and 16 in FIG. 14 is a consequence of the angular position of motion detectors 13 and 14 around the circumference of conduit 1. For example, if motion detector 14 was rotated 90° around the circumference of conduit 1 (not shown), then the non-flow phase relationship between signals 15 and 16 would be 180° (inverse phase) from each other. This fact can used to set a desired initial phase relationship between signals 15 and 16.

In the preferred exemplary embodiment of FIG. 1 a "natural" radial-mode of vibration was chosen for both the primary and the secondary frequencies since the power necessary to maintain a natural mode of vibration is normally less than that required to maintain a forced vibration that is not a natural mode. It is however not necessary to use a natural mode of vibration and in some circumstances it may be advantageous to force a flow conduit into a desired radial vibration at a non-natural frequency. For example, if a conduit material such as reinforced rubber or neoprene was used, the high damping coefficient of such materials would make a natural mode of vibration difficult to maintain, therefore a flow conduit of this nature could be forced to radially vibrate at a selected frequency.

Figure 11:
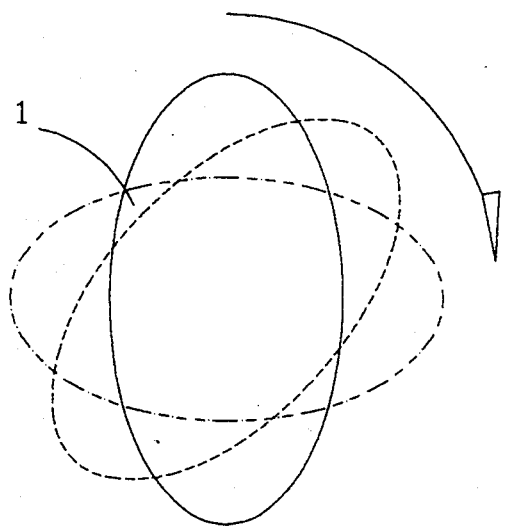
FIG. 11 is a cross-sectional representation of an alternate radial-mode of vibration to that shown in FIG. 10 with three sequential deflected shapes superimposed on each other. This mode is a two-lobe precessing mode.
Figure 12:
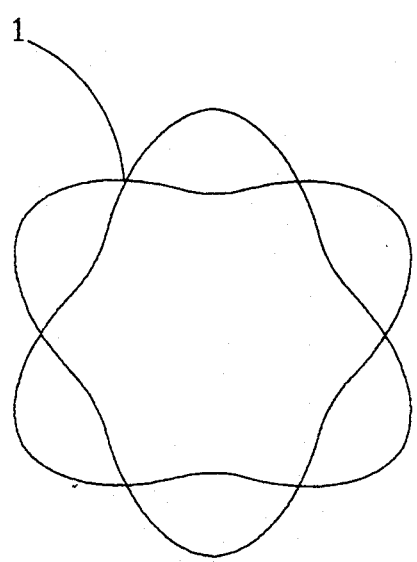
FIG. 12 is cross-sectional representation of an alternate radial-mode of vibration to that shown in FIG. 10 with two sequential deflected shapes superimposed on each other. This is a three-lobe mode.

Alternate modes of vibration for either the primary or the secondary modes can be employed to enhance various performance characteristics. Alternate radial-modes include the rotating elliptical mode of FIG. 11 where the elliptical cross-sectional shape is forced to precess around the conduit center-line never returning to a circular shape. In addition, a three lobed radial-mode as shown in FIG. 12 or a four lobed mode as shown in FIG. 13 could also be used as well as precessing versions of the three and four lobed modes (not shown), and others.

Figure 9:
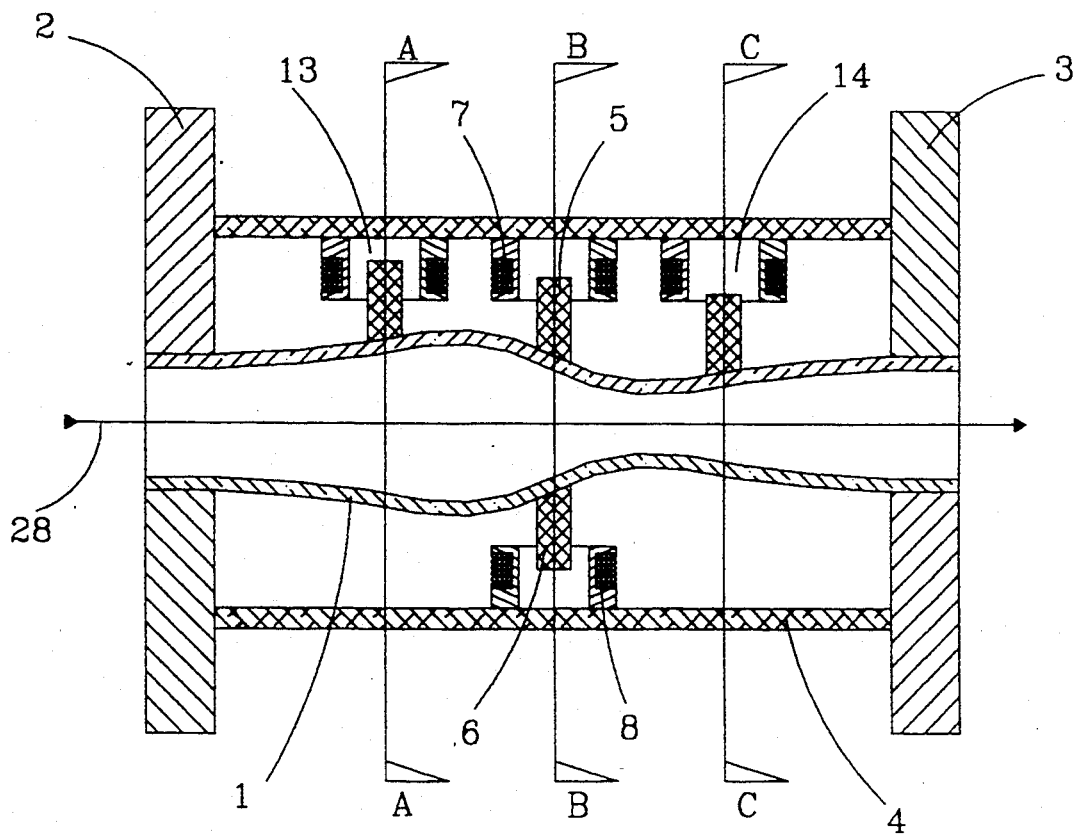
FIG. 9 is a cross-sectional view similar to that of FIG. 3 showing greatly exaggerated representative deflections of the flow conduit resulting from the Coriolis force distribution shown in FIG. 8.
Figure 9A:
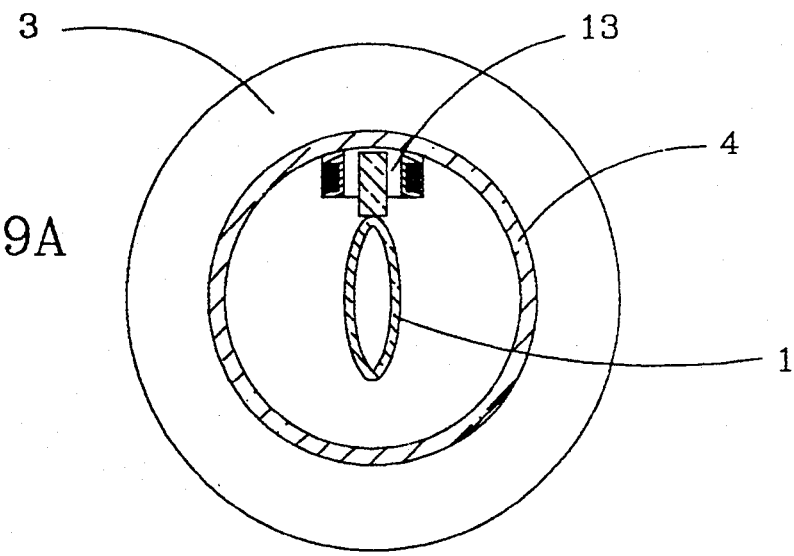
FIG. 9A is a cross-sectional view along section B—B of FIG. 9 showing the deformation of the cross-sectional shape of the flow conduit (greatly exaggerated) due to Coriolis forces, as the flow conduit passes through its center (normally undeformed) position.
Figure 9B:
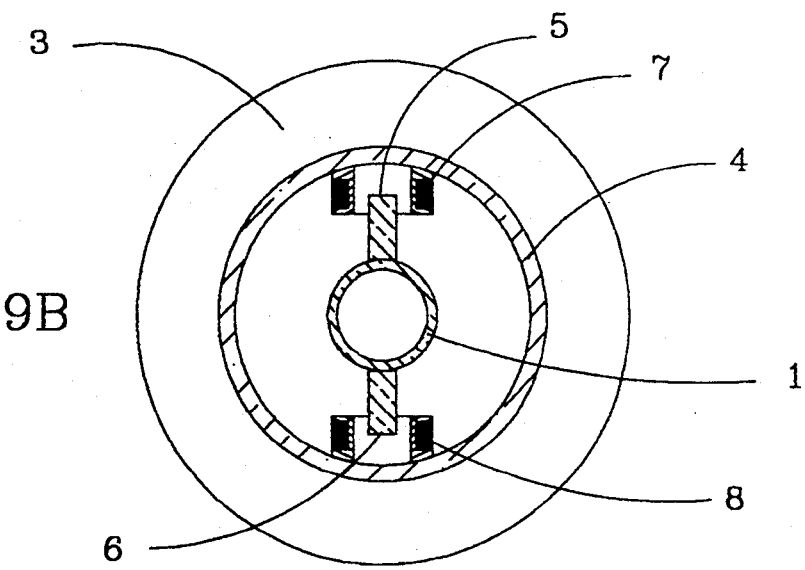
FIG. 9B is a cross-sectional view along section A—A of FIG. 9 showing essentially no deformation of the cross-sectional shape of the flow conduit due to Coriolis forces, as the flow conduit passes through its center position.
Figure 9C:
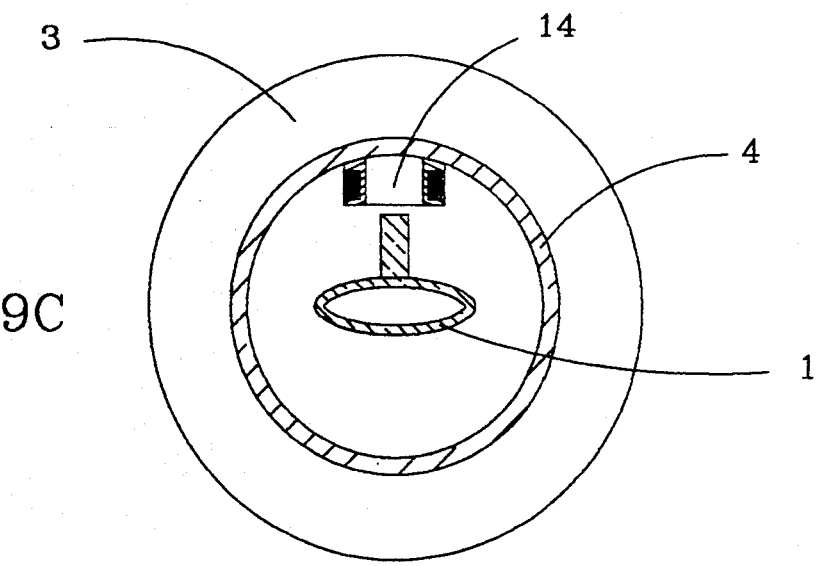
FIG. 9C is a cross-sectional view along section C—C of FIG. 9 showing the deformation of the cross-sectional shape of the flow conduit (greatly exaggerated) due to Coriolis forces, as the flow conduit passes through its center (normally undeformed) position.

In addition to radial-modes of vibration having increasing numbers of lobes around the perimeter of the flow conduit as just described, radial-modes which involve successive reversals of cross-sectional shape along the length of the flow conduit can also be used. FIGS. 9 through 9C show the deformed shape of flow conduit 1 due to mass flow rate, as previously explained. This deformed shape (response mode) is also representative of another natural mode of vibration of conduit 1 where the vertically elongated elliptical deformation at the fluid entry end (FIG. 9A) is reversed into the horizontally elongated deformation at the fluid exit end (FIG. 9C). Since this shape represents a natural mode of vibration, this fact can be used to enhance the frequency response of the structure and achieve greater sensitivity to mass flow rate. The amount of sensitivity gain that can be achieved in this way depends on the ratio of the driven frequency to that of the response mode frequency according to the following equation, the absolute value of which is plotted in FIG. 20.

$$\text{GAIN} = \frac{1}{1 - (D/R)^2} \quad (1)$$

Where;
D = Driven frequency
R = Response mode frequency

Figure 20:
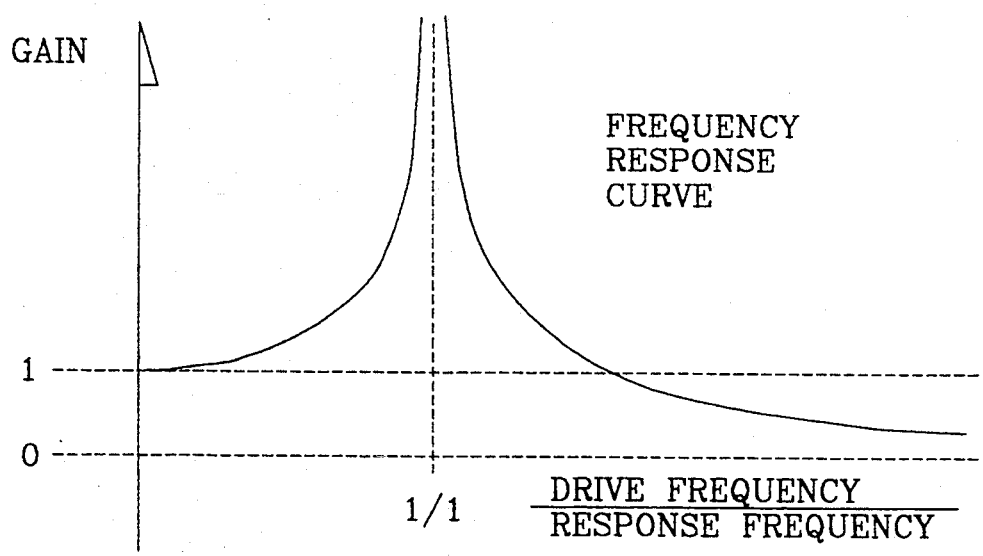
FIG. 20 is a graph of the frequency response curve and is representative of the absolute value of equation #1.
Figure 21:
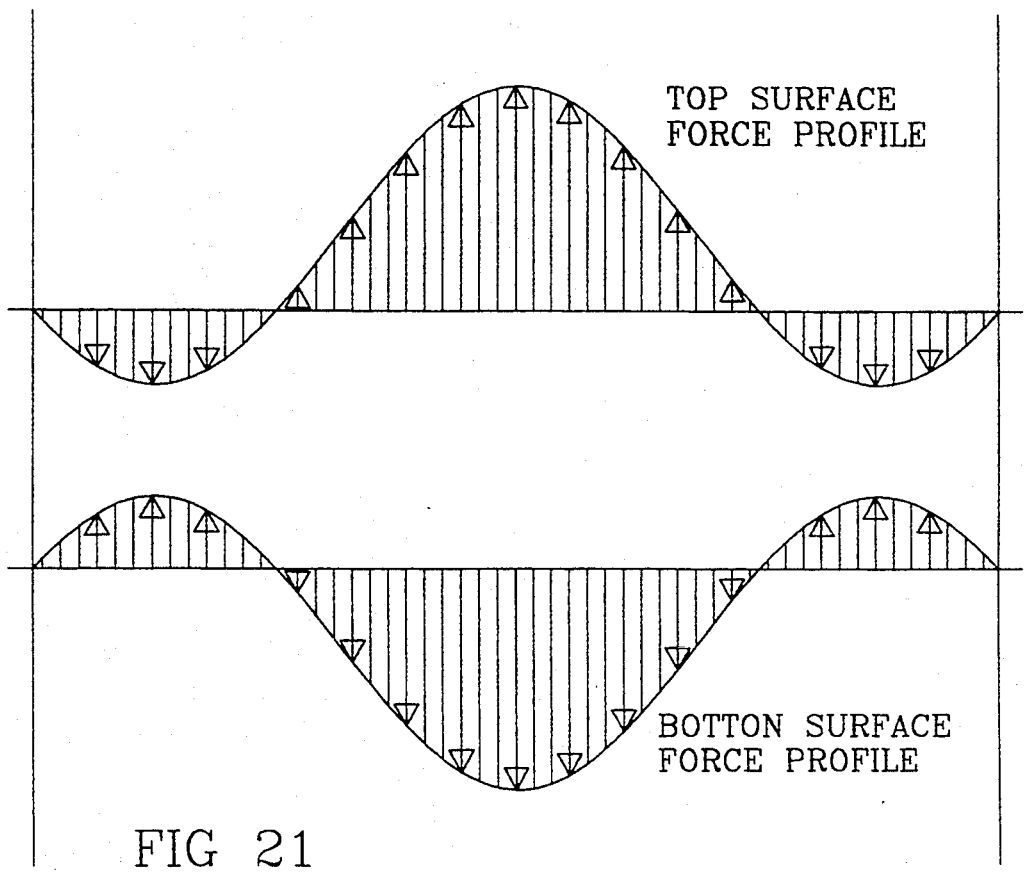
FIG. 21 is a representation of the Coriolis force distribution along the top and bottom surfaces of the flow conduit resulting from driving the flow conduit in a mode shape similar to that shown in FIG. 9.

According to equation 1, the gain will approach infinity as the driven frequency approaches the response mode frequency, which as a practical matter should be avoided due to instability. Operating on either side of the peak of FIG. 20 is acceptable. Operating on the right side of this peak means that the driven frequency is greater than the response mode frequency which can occur in the following way. If flow conduit 1 of FIG. 1 is forced to vibrate in the shape depicted in FIG. 9 as the primary driven mode, the induced Coriolis force distribution along the top and bottom surfaces of the conduit will be as shown in FIG. 21. Although this force distribution reverses its direction several times along the length of the conduit, since the ends of the conduit are fixedly attached and so are relatively inflexible, the center portion of the Coriolis force distribution will be the dominant factor with the overall effect that conduit 1 will deform into a shape similar to the earlier described primary driven mode as shown in FIGS. 2 through 7, proportionally related to mass flow rate. Since, for the preferred exemplary embodiment, the frequency of the mode shown in FIG. 9 (with one reversal in deflection direction along its length) is higher than the mode shown in FIGS. 2 through 7 (with no reversal), the ratio of the driven frequency to the response frequency is greater than one and thus constitutes working on the right side of the peak of FIG. 20. Another consequence of operating on the right side of the peak in FIG. 20 is that the phase shift of signals 15 and 16 is reversed so that signal 15 would precede signal 16 as a function of mass flow rate (not shown).

It is therefore anticipated that any radial-mode of vibration either natural or forced, can be used as the primary drive mode to create Coriolis forces which will deform the shape of flow conduit 1, proportionally related to mass flow rate. Similarly, any mode of vibration can be used as the secondary reference vibration to determine the pressure difference across the wall of the flow conduit, with the requirement that the secondary reference frequency must change as a function of fluid pressure by a different amount than the primary driven frequency. In addition it is preferable that the secondary frequency should not become synchronous with (an integer multiple of) the primary frequency over the expected range of the design.

A Unique consequence of the overall shape and operation of the preferred exemplary embodiment of FIG. 1 is that manifolds 2 and 3 can be designed as aerodynamically or hydrodynamically shaped fittings, and the device can be mounted open ended in a moving fluid stream such as on the wing of an airplane or the hull of a ship. In this arrangement, fluid flow through the meter can be related to its velocity relative to the surrounding fluid thereby creating a velocity meter.

Figure 17:
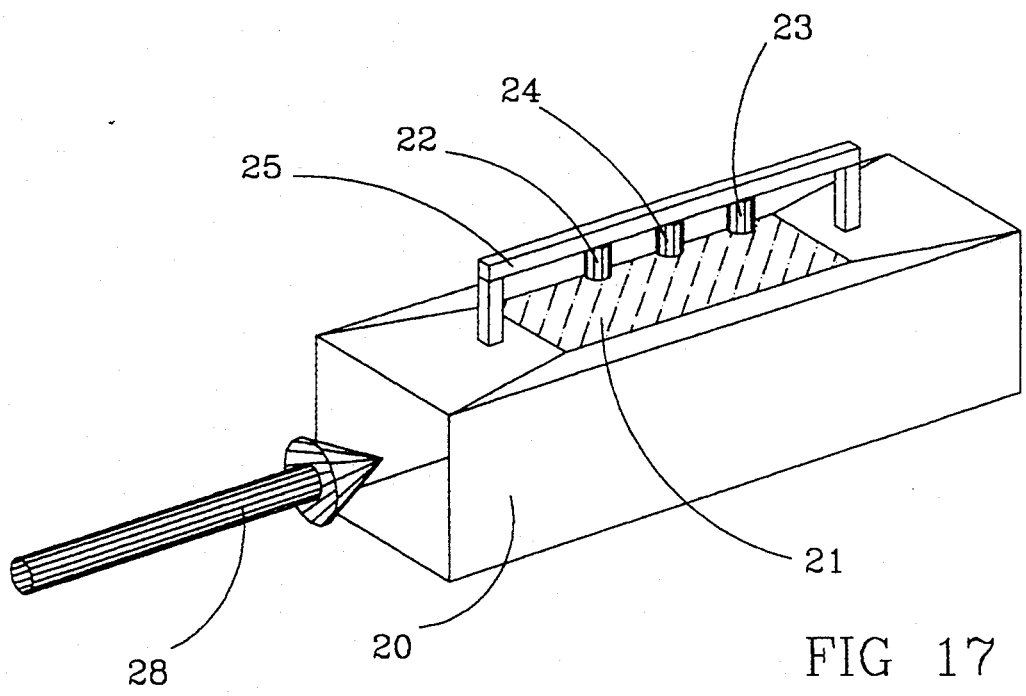
FIG. 17 is a perspective view of an alternate to the preferred exemplary embodiment of FIG. 1 using a vibrating flexible surface as part of a rectangular flow conduit perimeter to measure the mass flow rate in the conduit.
Figure 18:
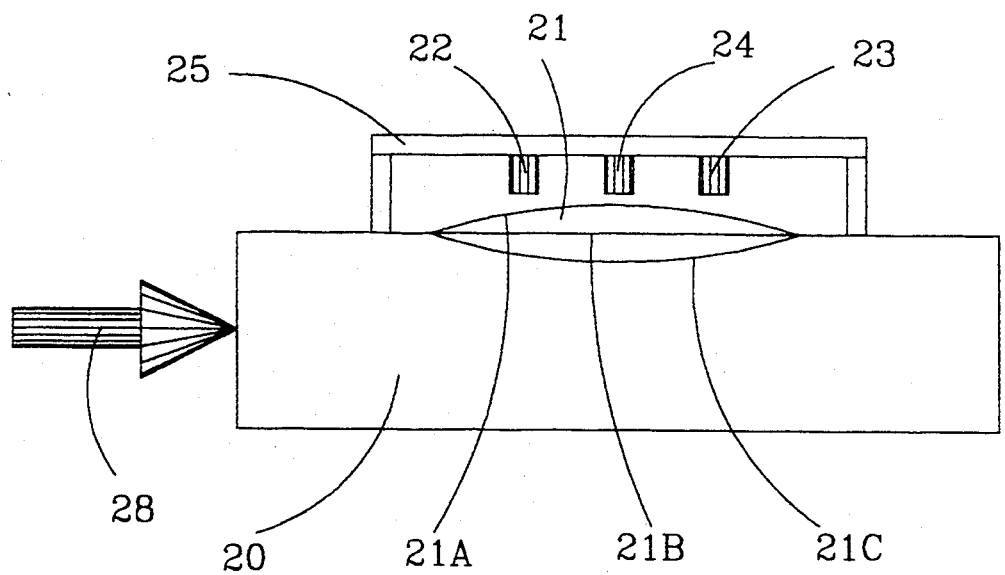
FIG. 18 is a cross-sectional view through the embodiment of FIG. 17 showing three sequential deflected shapes of the vibrating flexible surface with no fluid flow.

As an alternate to using a radial-mode of vibration involving the entire perimeter of the flow conduit, certain applications, especially low pressure, large thin-walled or non-circular flow conduits, or micro-flow meters etched or machined into bulk materials such as semiconductors or quartz, can be accommodated by vibrating only a portion of the flow conduit perimeter in a radial manner. The rectangular flow conduit of FIG. 17 is well suited for low pressure applications such as air flow in duct systems, however, flow conduits that are large in comparison with their wall thickness, and conduits with flat sides can be impractical to vibrate in radial-modes involving the entire perimeter. Similarly, flow conduits that are formed into bulk materials such as silicon or quartz, will have flow conduit sides which are essentially rigid therefore not able to be vibrated in a radial-mode of vibration involving the entire conduit perimeter. The design of a Coriolis mass flow rate meter according to the present invention for these applications can therefore be accommodated by radially vibrating only a portion of the flow conduit perimeter to create the requisite Coriolis force distribution necessary to measure flow rate. In the embodiment of FIG. 17, flow conduit 20 is an example of an ordinary sheet metal rectangular air duct into which is installed flexible surface 21 preferably made of a strong flexible material such as carbon steel sheet metal. Surface 21 is flexibly attached to conduit 20 at its fluid entry and exit ends, and essentially free along it's sides to accommodate radial vibration, except that the sides can be sealed from leakage with a flexible membrane (not shown). Surface 21 is forced to radially vibrate by electromagnetic motion driver 24 which is fixedly attached to mounting bar 25 as shown in FIG. 17. The radial vibration of surface 21 is shown in FIG. 18 at its upper 21A, middle 21B and lower 21C positions of its vibration.

Figure 8:
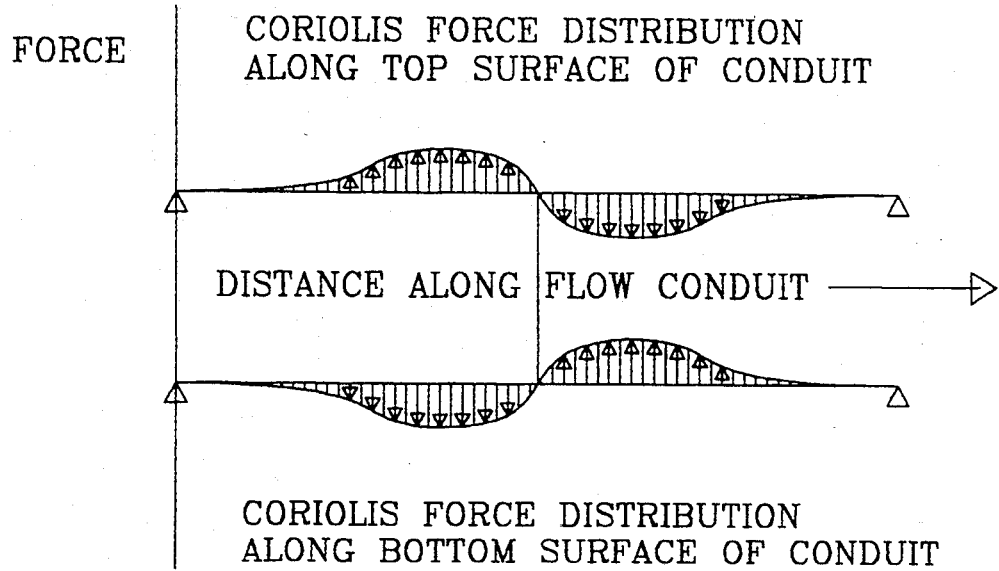
FIG. 8 is a graph of the Coriolis force distribution that would be created along the top and bottom surfaces of the flow conduit from mass flow rate, as the flow conduit passes through its undeflected center position as in FIG. 3.
Figure 19:
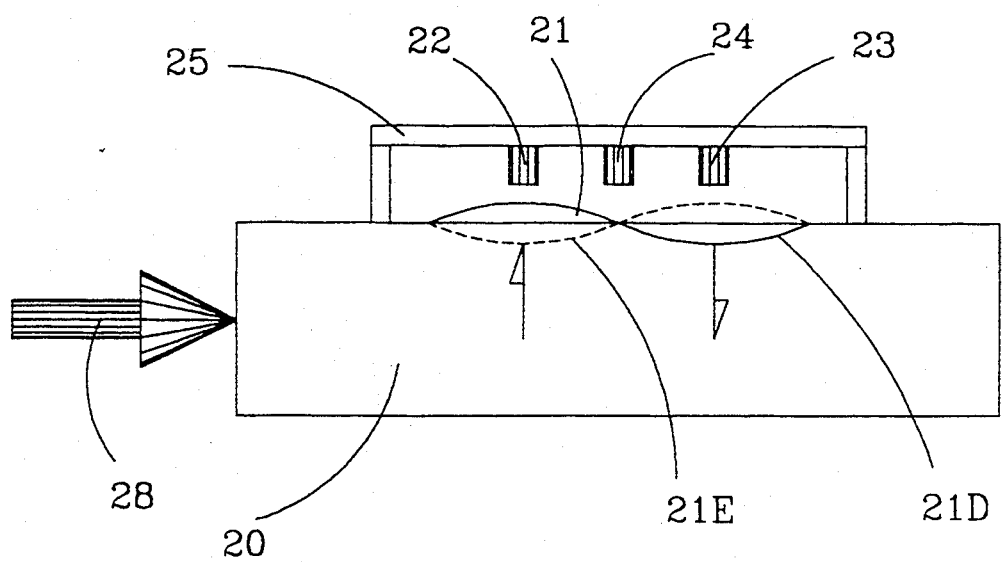
FIG. 19 is a cross-sectional view through the embodiment of FIG. 17 showing the deflected shape of the vibrating flexible surface due to Coriolis forces with fluid flowing through the flow conduit.

The combination of the radial vibration of surface 21 and fluid flow 28 will cause a Coriolis force distribution along the inner face of surface 21 similar to the top surface Coriolis force distribution shown in FIG. 8. This will cause surface 21 to deform slightly into a sine-wave like shape 21D as shown in FIG. 19, as it passes downward through it's normally flat center position, then deforming into an inverted sine-wave like shape 21E as shown in FIG. 19, as it passes upward through it's normally flat center position, thereby causing a difference in the signals produced by motion detectors 22 and 23. One measurable effect of this deformation is that the motion of surface 21 becomes delayed in time at the fluid entry end of conduit 20, and advanced in time at the fluid exit end of conduit 20 as a function of mass flow rate through conduit 20. Motion detectors 22 and 23 are fixedly attached to mounting bar 25 at positions separated from each other by some distance along the length of surface 21. Signals from motion detectors 22 and 23 (not shown) will therefore be shifted in time from each other by an amount related to the mass flow rate of process-fluid in conduit 20 analogous to signals 15 and 16 in FIG. 15. It is anticipated that the flexibility of surface 21 and thus the sensitivity of the device to mass flow rate, can be enhanced by proper configuration and material choice of flexible surface 21, or by mounting surface 21 on flexural supports such as diaphragms, bellows, hinges, fabric and the like. Some possible materials that can be used for surface 21 are sheet metal, fiberglass, plastic, rubber, latex, glass, and others.

As an alternate to using a single vibrating surface along the perimeter of flow conduit 20, multiple surfaces can be employed and vibrated in conjunction with each other to more fully involve the perimeter of the flow conduit.

Figure 22:
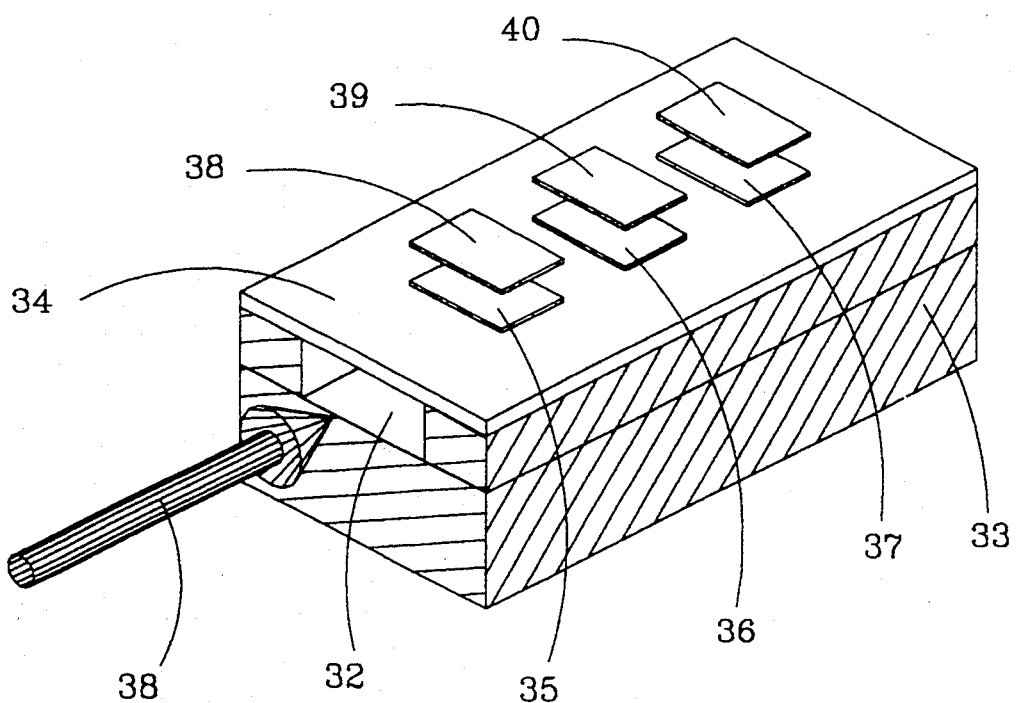
FIG. 22 is an alternate exemplary embodiment of the present invention employing a flow conduit that has several rigid sides and a flexible surface that is vibrated.

FIG. 22 depicts an alternate embodiment of the present invention in which flow conduit 32 is etched or machined into semiconductor material 33, and covered with a flexible surface 34 on which is deposited electrodes 35, 36, and 37 positioned over flow conduit 32. Electrodes 38, 39, and 40 are positioned on a rigid surface (not shown) above and to interact with electrodes 35, 36, and 37 respectively. Electrode pair 36 and 39 are then electrically excited to force flexible surface 34 to vibrate similar to that shown in FIG. 18. Electrode pairs 35 and 38, and 37 and 40 are then used as capacitive motion detectors to sense the vibration of surface 34. In this configuration, the time relationship between the motion sensed at the fluid entry end of surface 34 will be delayed from the motion sensed at the fluid exit end of surface 34 by an amount that is functionally related to mass flow rate through the conduit. It is anticipated that the flexibility of surface 34 can be enhanced by etching or machining thinner or weak areas associated with it to facilitate flexing motion.

It is anticipated that the methods herein described for the present invention can be employed on flow conduits with many cross-sectional shapes including circular, oval, elliptical, convoluted, irregular, rectangular, polygonal, and others. In addition, the cross-sectional shape of a flow conduit can be permanently deformed along its length to enhance its flexing characteristics and thus its sensitivity to mass flow.

What is claimed is:

1. An apparatus for measuring a mass flow rate of a fluid in a flow conduit, comprising:
   means for inducing a rotating elliptical radial mode vibration in said conduit, said rotating elliptical radial mode vibration causing deformation of said conduit; and
   means for measuring a change in said deformation.

2. The apparatus as recited in claim 1 wherein said measuring means comprises a first motion detector.

3. The apparatus as recited in claim 2 wherein said measuring means comprises a second motion detector.

4. The apparatus as recited in claim 2 wherein said change is determined by measuring a change in time relation of said deformation.

5. The apparatus as recited in claim 2 wherein said change is determined by measuring a change in amplitude of said deformation.

6. The apparatus as recited in claim 2 further comprising:
   an inlet manifold affixed to an end of said flow conduit; and
   an outlet manifold affixed to an opposite end of said conduit.

7. The apparatus as recited in claim 2 further comprising:
   a pressure-tight case, integral with said conduit, defining a pressure-tight chamber about said conduit, said chamber containing a prescribed amount of pressure.

8. The apparatus as recited in claim 7 further comprising:
   an inlet manifold affixed to an end of said conduit and defining a first wall of said pressure-tight chamber; and
   an outlet manifold affixed to an opposite end of said conduit and defining a second wall of said pressure-tight chamber.

9. The apparatus as recited in claim 8 wherein said pressure-tight case reduces axial stress on said conduit.

10. The apparatus as recited in claim 7 further comprising:

a first temperature sensor in thermal communication with said conduit; and a second temperature sensor in thermal communication with said case.

11. The apparatus as recited in claim 10 further comprising means for isolating vibration associated with said conduit to a selected portion of said conduit.

12. The apparatus as recited in claim 1 further comprising means for reducing axial stress associated with said conduit.

13. The apparatus as recited in claim 1 wherein said deformation comprises a plurality of lobes around a circumference of said conduit.

14. The apparatus as recited in claim 1 wherein a time relation of said deformation reverses along a length of said conduit.

* * * * *